US006998254B1

(12) United States Patent
Raspe et al.

(10) Patent No.: US 6,998,254 B1
(45) Date of Patent: Feb. 14, 2006

(54) USE OF ROR FOR RECEPTORS FOR SCREENING SUBSTANCES USEFUL FOR THE TREATMENT OF ATHEROSCLEROSIS

(75) Inventors: Eric Raspe, Mouscron (BE); Yves Bonhomme, Charbonniees les Bains (FR)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/646,924

(22) PCT Filed: Mar. 24, 1999

(86) PCT No.: PCT/EP99/02001

§ 371 (c)(1),
(2), (4) Date: Sep. 25, 2000

(87) PCT Pub. No.: WO99/50660

PCT Pub. Date: Oct. 7, 1999

(30) Foreign Application Priority Data

Mar. 29, 1998 (FR) .................................... 98 03475

(51) Int. Cl.
*C12P 21/06* (2006.01)
*C12Q 1/68* (2006.01)
*A01N 43/04* (2006.01)

(52) U.S. Cl. ............................ 435/69.1; 435/6; 514/44

(58) Field of Classification Search .................... 435/6, 435/69.1; 536/23.31; 514/44
See application file for complete search history.

(56) References Cited

OTHER PUBLICATIONS

Accession No. X13367. Human DNA for apolipoprotein C-III 5'-flank, 1997.*
Reue K et al. Human apolipoprotein CIII gene expression is regulated by positive and negative cis-acting elements and tissue-specific protein factors. J. Biol Chem., vol. 263, No. 14, pp. 6857-6864, 1988.*

* cited by examiner

*Primary Examiner*—Jeffrey Fredman
*Assistant Examiner*—Suryaprabha Chunduru
(74) *Attorney, Agent, or Firm*—Millen, White, Zelano & Branigan, P.C.

(57) ABSTRACT

The subject of the present invention is the use of the ROR receptors and/or of their response element or alternatively of a functional equivalent thereof for the screening of substances having antiatherosclerotic properties. The invention also relates to the methods of screening substances having antiatherosclerotic properties using the ROR receptors and/or their response elements. The invention also relates to the use of the methods of screening according to the present invention in order to characterize, justify and claim the mechanism of action of substances having antiatherosclerotic properties using the ROR receptors and/or their response elements as well as their effects on apo C-III.

8 Claims, 17 Drawing Sheets

Figure 1:
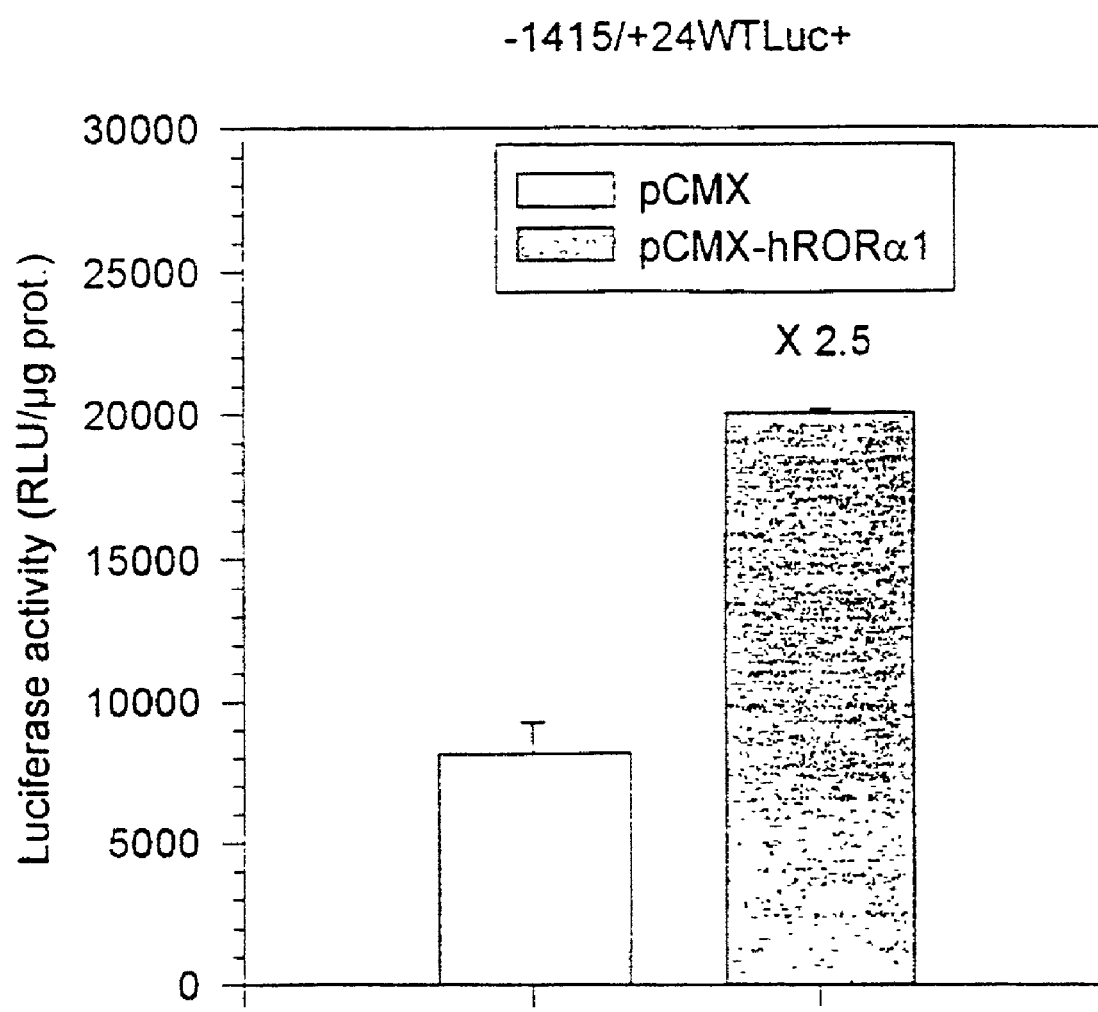

USE OF ROR FOR RECEPTORS FOR SCREENING SUBSTANCES USEFUL FOR THE TREATMENT OF ATHEROSCLEROSIS

The present invention relates to the use of ROR receptors for screening compounds having an anti-atherosclerotic activity. The invention relates more particularly to the different methods of screening which make it possible to identify substances useful for the treatment and/or prevention of atherosclerosis. The invention also relates to the use of the substances thus identified for the preparation of therapeutic compositions intended for the treatment and/or prevention of atherosclerosis.

The invention also relates to the use of screening tests to characterize, justify and claim the mechanism of action of substances for the preparation of therapeutic compositions intended for the treatment and/or prevention of atherosclerosis.

The orphan receptors ROR (retinoic acid receptor related orphan receptor), also called RZR (17–19), constitute a subfamily of nuclear receptors for which no ligand has been identified.

The ROR receptors exist in three forms, ROR, α, β, γ (17, 19, 20). The ROR receptors bind in monomeric or dimeric form, each to a specific response element consisting of a sequence rich in A/T preceding a sequence of the PuGGTCA type (17, 21, 22), and modulate the transcription of their target genes.

Following alternative splicing, the RORα gene leads to 4 isoforms α1, α2, α3 and RZRA (17–19) which differ by their N-terminal domain and show DNA recognition and distinct transactivating properties (17).

ROR receptors will be understood to mean hereinafter ROR as well as RZR and RORγ, as well as, unless otherwise stated, the different isoforms of RORα, α1, α2, α3 and RZRA. The invention relates to any mammalian ROR receptor but the human ROR receptors are more particularly envisaged.

The discovery of ligands for the family of orphan receptors in general and of ROR receptors in particular and the definition of their role in the transcriptional properties of ROR constitutes a research theme of fundamental importance for the understanding of the phenomena of regulation of genes, especially of the genes involved in certain pathological conditions (DN & P 9(3), April 1996).

Melatonin has been proposed as a ligand for a receptor of the family of orphan nuclear receptors ROR/RZR (51). Likewise, PCT international patent application published under number WO 95/27202, based on the teaching of the article by Becker-André et al., describes the use of RZR/RORα receptors for the screening of substances possessing a melatonin, antiarthritic, antitumour or antiautoimmune type activity.

However, recent studies (52) challenge the effective capacity of melatonin to act as a ligand for the family of nuclear receptors RZR/RORα.

There is therefore at present no substance whose capacity to act as a ligand for a receptor of the RZR/RORα family is clearly established.

Several genes whose expression is regulated by the nuclear receptors are known in the prior art. Among them, there may be mentioned recent work showing that the RORα receptors are involved in the regulation of the expression of the apo A-I gene in mice and rats (53).

Recently, a substantial hypoalphalipopro-teinaemia was observed in mice whose RORα gene is truncated and leads to the synthesis of a nonfunctional protein (sg/sg mouse).

Furthermore, these mice suffer from a more pronounced atherosclerosis than the wild-type SG/SG mice when they are subjected to a proatherogenic regime. This exacerbated response is attributed to the increase in the inflammatory response in the sg/sg mice and to the substantial reduction in the expression of the apo A-I gene (54).

Figure 13:
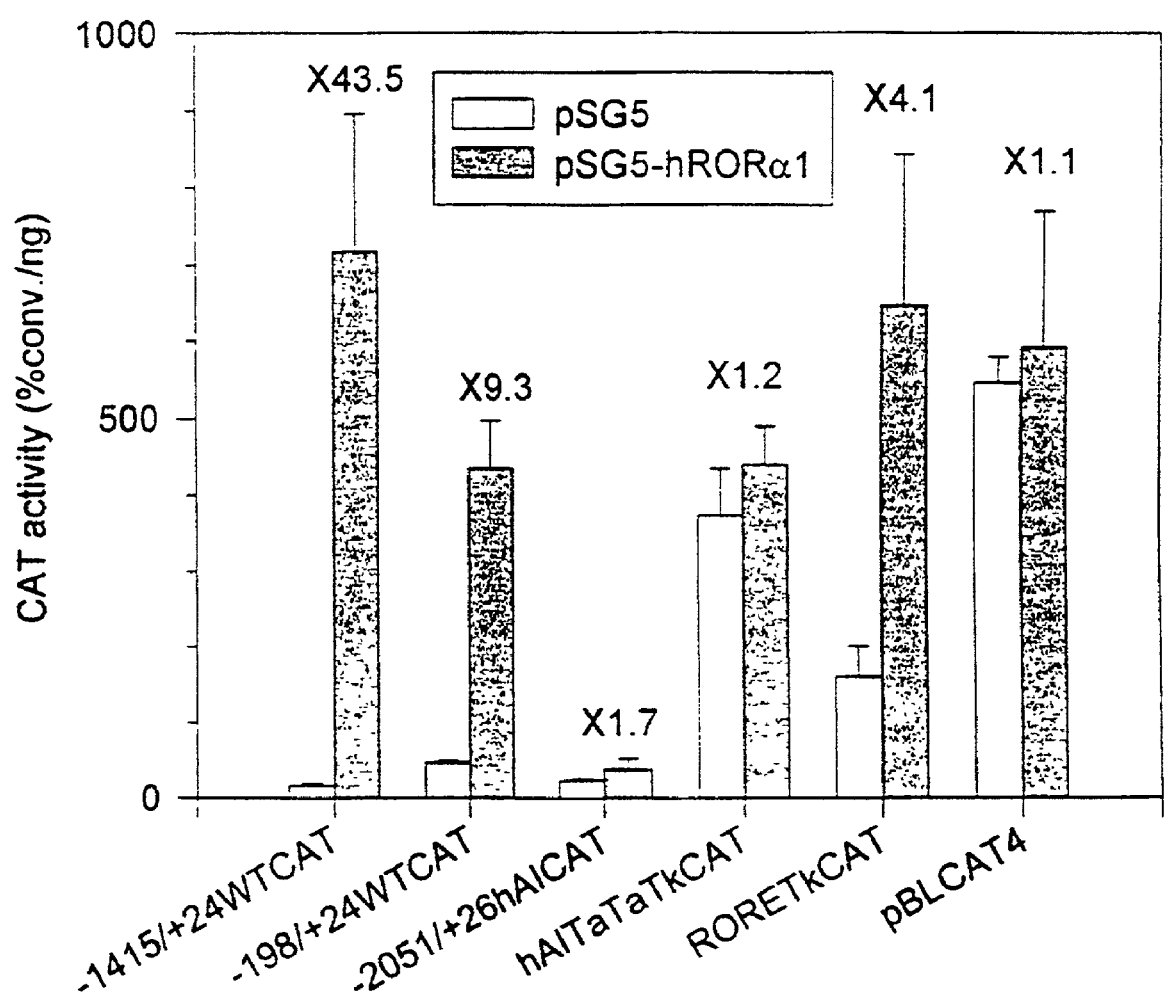

However, the results obtained in mice are not directly transposable to humans because of the fact that the human gene for APO A-I appears to be insensitive to ROR, which is illustrated by the results obtained by the applicant and presented in the annex (FIG. 13). Indeed, the sequences of the promoters of the genes for murine and human APO A-I diverge at the level of the site recognized by ROR.

The inventors have now discovered, surprisingly, that the RORα receptors are involved in the regulation of the expression of the apo C-III gene both in mice and in humans.

Apolipoprotein C-III is a glycoprotein of 79 amino acids which is synthesized in the liver and to a lesser degree in the intestine. However, apolipoprotein C-III, also designated hereinafter apo C-III, is a key product of the plasma metabolism of triglycerides. It has been shown that the plasma concentrations of apo C-III are correlated to the plasma level of triglycerides, both in a normal population and in hypertriglyceridaemic patients (1–4).

In addition, it has been shown that the apolipoproteins and more particularly apo C-III, play a major role in the appearance of cardiovascular diseases. Indeed, the increase in the apo C-III concentrations in the lipoprotein particles containing apo B (apo C-III-LpB) is associated with an increase in the risk of coronary cardiac diseases (5).

It has also been reported that an apo C-III deficiency caused an increase in the catabolism of the VLDL particles, whereas an increase in the synthesis of apo C-III was observed in patients with hypertriglyceridaemia (6, 7). Apo C-III is therefore directly linked to the catabolism of the plasma triglycerides.

Moreover, genetic studies have demonstrated an association between certain polymorphisms of the apo C-III gene and high plasma concentrations of apo C-III and triglycerides (8, 9). Likewise, the overexpression of human apo C-III in transgenic animals has as consequence the development of a hypertriglyceridaemia whereas elimination of the endogenous apo C-III gene by homologous combination in mice leads to the reduction of the plasma concentrations of apo C-III and protects the animals against post-prandial hypertriglyceridaemia (10, 11). In addition, the crossing of mice carrying the human apo C-III transgene with heterozygous mice deficient in LDL receptors results in the acquistion of several characteristics of combined familial hyperlipidaemia and causes increased sensitivity to atherosclerosis: the apo C-III gene is capable of inducing the development of atherosclerosis (55).

In addition, the results of studies in vitro and in vivo indicate that apo C-III acts mainly by delaying the catabolism of particles rich in triglycerides through inhibition of their attachment to the endothelial surface and their lipolyses by lipases specific for lipoproteins, as well as by interfering with the clearance of residual particles in plasma by the apo E receptor (12–16).

Recently, it has appeared clearly that, in addition to the plasma levels of cholesterol and its particulate distribution, the plasma level of triglycerides is a risk factor independent of the development of coronary diseases (56). Indeed, several studies have demonstrated an association between the plasma level of triglycerides and the extent and severity of coronary diseases diagnosed by angiography (58). Finally, recent results of epidemiological studies and of clinical trials strongly suggest that a high level of circulating triglycerides constitutes a risk factor independent of coronary diseases (57).

The reduction in the expression of apo C-III therefore represents a relevant target in order to identify substances possessing antiatherogenic properties.

The present invention is based on the demonstration of a new property of the ROR receptors as positive regulator of the transcription of the apo C-III gene both in mice and in humans. These results are in particular based on the observation made by the inventors that the expression of the apo C-III gene was severely repressed in staggerer mice known to carry a deletion for the RORα gene causing the synthesis of a nonfunctional protein (27).

These results have made it possible to establish that the ROR receptors constitute a new factor for regulating the expression of genes involved in the catabolism of triglycerides and therefore in atherosclerosis.

Consequently, the aim of the invention is to offer means which make it possible to identify new ligands for the RORα receptors capable of modulating the transcription of the apo C-III gene and therefore capable of influencing atherosclerosis, both as regards its prevention and its treatment.

The present invention therefore relates to the use of the ROR receptors and/or of their response elements or alternatively of a functional equivalent thereof for the screening of substances having antiatherosclerotic properties.

The present invention also relates to the use of the ROR receptors and/or of their response elements or alternatively of a function equivalent thereof for the characterization, justification and claiming of the mechanism of action of substances having antiatherosclerotic properties.

For the purposes of the present invention, ROR receptor designates all the α, β and γ isoforms of the ROR family.

Functional equivalent of ROR is understood to mean any protein having both:
  a binding site possessing a selectivity comparable to that of RORα for a given ligand for it, and
  a DNA binding site recognizing the same response element as RORα or a response element possessing a related nucleic acid sequence.

Functional equivalent of ROR is also understood to mean a chimeric protein having:
  a ligand binding site having a selectivity comparable to that of RORα for a given ligand for it, and
  a DNA binding site recognizing a response element of a reporter gene cloned upstream of a heterologous promoter, or a protein domain which allows easy purification of the chimera and its specific binding to defined templates such as for example the Maltose Binding Protein (MBP) or glutathione S-transferase (GST). The latter type of chimera has often been used (42). It has the advantage of allowing purification of the protein in one step by affinity column or of specifically separating it by simple procedures well known to persons skilled in the art (coupling to magnetic beads or to resins coated with glutathione, elution with maltose or glutathione, and the like).

Functional equivalent of the response element of the ROR receptor is understood to mean any nucleic acid sequence to which the RORα receptor can bind and more particularly a sequence derived from the response element of the RORα receptor.

The RORα receptor and the response element of the RORα receptor are more particularly preferred in the use of the invention.

The hRORα receptor, the messenger RNA for hRORα and the response element of the hRORα receptor are more particularly preferred in the use of the invention.

The subject of the present invention is therefore a first type of method of screening substances useful in the treatment of lipid metabolism dysfunctions consisting in bringing the test substance into contact with a receptor of the ROR family and/or a response element of the ROR receptor and/or a nuclear factor capable of functionally coupling ROR to the RNA polymerase complex, or a functional equivalent thereof, and then in measuring by any appropriate means:
  the binding of the said substance to the ROR receptor and/or its functional equivalent or the binding of the complex formed of the said substance and the ROR receptor to its response element and/or to a nuclear factor capable of functionally coupling ROR to the RNA polymerase complex, and/or
  the modulation of the transcriptional activity of a gene placed under the control of a promoter comprising the said response element.

The measurement of the binding of the substance to the ROR receptor and/or its functional equivalent or the binding of the complex formed of the said substance and the ROR receptor to its response element may be carried out by any direct or indirect methods known to persons skilled in the art, such as those using a reporter gene, binding tests, and the like.

In the same manner, the measurement of the modulation of the transcriptional activity of a gene placed under the control of a promoter comprising the ROR response element may be carried out by any direct or indirect methods known to persons skilled in the art.

In order specify the use of the substance tested in the treatment of lipid metabolism dysfunctions, the method of the invention comprises an additional step aimed at determining by any appropriate means the effect of the said substance on the expression of apo C-III. The determination of the effect of the substance tested on the expression of apo C-III may be carried out by any direct or indirect methods known to persons skilled in the art, such as transfection, analysis of the mRNAs in vitro or on models in vitro and in vivo.

A first example of the method of screening according to the present invention comprises the following steps:
  a) a cellular host is transfected with a DNA fragment encoding an ROR receptor or one of its functional equivalents,
  b) the host in step (a) is cotransfected with a construct comprising a response element of the said ROR receptor and at least one reporter gene,
  c) the expression of the reporter gene in the presence of the test substance is measured by any appropriate means.

The response element used in step (b) may for example consist of the fragment of the apo C-III promoter between positions 1415 and +24.

Any reporter gene which makes it possible to measure the activity of nuclear receptors on the sequence comprising their response element may be used in the method of screening according to the invention. Among these, there may be mentioned, without being exclusive, for example, the gene for chloramphenicol acetyltransferase (CAT), the gene for the luciferase from firefly (Luc) or from Renilla (Ren), the gene for secreted alkaline phosphatase (Pas) or that for beta-galactosidase (β-Gal). The activity of the proteins encoded by these genes can be easily measured by conventional methods and makes it possible to know the effect of the nuclear receptors or the expression of the genes by measuring the quantity of proteins produced and/or their enzymatic activity.

It is understood that suicide genes for selection (such as for example thymidine kinase of the herpes simplex virus (44)) or genes for positive selection (such as for example genes for resistance to an antibiotic or to nutritional deficiencies) can also be considered as reporter genes because of the fact that cellular survival in selective medium is a reflection of the activity of these genes.

The action of the ROR receptors and more particularly of the hROR$\alpha$1 receptor on the gene for apo C-III reported by the inventors of course makes it possible to use, in the constructs of the invention and the methods of screening using them, the gene for apo C-III as reporter gene.

In the method of screening of the invention, cellular host is understood to mean any cell type appropriate for the expression of the above genes, such as in particular mammalian, bacterial or yeast cells or alternatively insect cells. The vectors used are of course appropriate for the cell type transfected; there may be mentioned plasmids, viruses or artificial chromosomes.

Another example of this first type of method of screening according to the invention comprises the following steps:
  a) a plasmid is created which comprises several copies of a response element recognized by ROR such as for example the consensus site described by M. Lazar (43), the response element(s) identified in the apo C-III promoter. These copies of the response element are cloned upstream of a strong heterologous promoter such as the thymidine kinase promoter of the herpes simplex virus, or a homologous strong promoter such as the apo C-III promoter. This promoter is itself placed so as to control the expression of a reporter gene such as luciferase, CAT, alkaline phosphatase, $\beta$-galactosidase and the like.
  b) the construct of step (a) is transfected into cells which express ROR naturally or artificially, that is to say after transient cotransfection of an expression vector or creation of a stable line expressing ROR.
  c) the host of step (b) is incubated in the presence of the test substance.
  d) the activity of the reporter gene is measured by any appropriate means.

An additional example of this first type of method comprises the following steps:
  a) a plasmid is created which comprises several copies of a response element recognized by ROR cloned upstream of a promoter which controls the expression of a suicide gene for selection such as for example the activator of a toxic prodrug such as thymidine kinase of the herpesvirus (44).
  b) the construct of step (a) is transfected into a cellular host.
  c) the host of step (b) is cotransfected with the aid of a vector expressing ROR.
  d) The host of step (c) is incubated in the presence of the test substance.
  e) Cellular survival in the presence of the toxic prodrug is measured by any appropriate means.

The toxic prodrug may be for example ganciclovir.

Yet another example of this first type of method comprises the following steps:
  a) a plasmid is created which comprises several copies of a response element recognized by the yeast nuclear factor Gal4 cloned upstream of a strong promoter such as for example the thymidine kinase promoter of the herpes simplex virus, which controls the activity of a reporter gene such as luciferase, CAT, alkaline phosphatase, $\beta$-galactosidase, growth hormones, toxic prodrug activators (for example thymidine kinase of the herpes simplex virus) and the like,
  b) the plasmid is created from a chimera which comprises the DNA binding domain of Gal4 and the DEF domains of ROR which are the ROR domains to which the ligands bind,
  c) the plasmids obtained in steps (a) and (b) are cotransfected into a cellular host,
  d) the host of step (c) is incubated in the presence of the test substance.

The activity of the reporter gene is measured by any appropriate means.

The DEF domains of the nuclear receptors differ between the different members of this family. They comprise sequences involved in the transactivation of transcription and the binding of the ligands and of the cofactors. The DEF domains of ROR are combined with the Gal4 fragment which contains the first 147 amino acids of Gal4 in order to create a chimera Gal4-ROR which binds to the Gal4 response element and whose transcriptional activity depends on the ligands and/or cofactors for ROR (43).

The basic activity of the chimera may be increased by the insertion of a DNA fragment which encodes all or part of the VP16 protein (45).

An additional example of this first type of screening method consists in the quantitative evaluation of the effects of the compounds tested in systems of the "double hybrid" type in yeasts or other cells which comprise the ROR fragments which interact with cofactors and the corresponding fragments of the cofactors (e.g.: N—COR, SMRT (43)) which couple ROR to the transcription machinery and in particular to the RNA polymerise complex.

Another example of the first type of the method of screening according to the invention consists in quantitatively evaluating the effects of the compounds tested on the capacity for interaction in vitro between the full-length ROR protein or some of its fragments and cofactors or some of their fragments by any technique known in the state of the art (for example by the CARLA approach developed for the screening of the PPAR ligand (42), resonance fluorescence energy transfer measurement method).

A final example of the first type of method of screening according to the invention consists in transforming a host cell as defined above with a construct carrying a gene encoding the ROR receptor and its functional equivalent and/or a response element of the ROR receptor, and then in using the said cellular hosts or extracts thereof in binding tests based on the competitive displacement between a cold ligand and a labelled ligand.

The subject of the present invention is also the substances selected by a method of screening according to the present invention, as well as the use of these substances for the preparation of a composition, especially a pharmaceutical composition, repressing the expression of apo C-III and therefore intended for the treatment of lipid metabolism dysfunctions in humans or animals. Indeed, the compounds having such properties are selected on the basis of their capacity to repress the expression of apo C-III, and may be ROR ligands or ROR analogues, whose properties are demonstrated either directly from the level of expression of apo C-III or through the expression of a reporter gene, or alternatively by their capacity to form a complex with the ROR receptor.

The invention therefore relates more generally to the use of a substance capable of modulating the expression of apo C-III for the preparation of a composition, especially a pharmaceutical composition, useful for the treatment and/or prevention of lipid metabolism dysfunctions linked to apolipoprotein C-III in humans or animals. More particularly, the invention relates to the use of a substance capable of binding to the ROR receptor or to its response element for the preparation of a pharmaceutical composition useful for the treatment and/or prevention of lipid metabolism dysfunctions in humans or animals.

The subject of the present invention is also the use of the methods of screening according to the present invention to characterize, justify and claim the mechanism of action of substances capable, by binding to and by modulating the activity of ROR, of modulating the expression of apo C-III for the preparation of a composition, especially a pharmaceutical composition, useful for the treatment and/or prevention of lipid metabolism dysfunctions linked to apolipoprotein C-III in humans or animals.

Other advantages and characteristics of the invention will appear from the following examples describing the activation of the apo C-III promoter by the human RORA receptor.

I. Methods

1. Cell Culture

The HepG2 (human hepatoma) line is obtained from E.C.A.C.C. (Porton Down, Salisbury, UK) whereas the RK13 (rabbit kidney) cells were offered by C. Lagros (laboratory of Prof. Stéhelin). These lines were maintained under standard culture conditions (Dulbecco's modified Eagle's minimal essential medium), supplemented with 10% foetal calf serum, incubation at 37° C. under a humid atmosphere of 5% $CO_2$/95% air). The culture medium is changed every two days.

2. Construction of the Recombinant Plasmids

The activity of the promoter of the apo C-III gene was studied according to conventional techniques using reporter genes. The constructs −1415/+24hCIIIWT-CAT, −1415/+24hCIIIC3P5'KO-CAT, −198/+24hCIIIWT-CAT and −198/+24hCIIIC3P5'KO-CAT which comprise fragments of the promoter of the human gene for apo C-III, which are of the wild type or mutated at the level of the half-site TGGGCA present at position 5' of the C3P site cloned upstream of the CAT reporter gene have been previously described (61). The construct RORETkCAT which comprises a copy of the hRORα consensus response element has been previously described (53). The fragment −2051/+26 of the human gene for apo A-I was excised with the aid of the enzyme KpnI from a clone isolated from a genomic DNA library in γ_Charon 4A, made blunt by treatment with the Klenow fragment of DNA polymerase, and cloned before the CAT reporter gene into the vector pBLCAT5, at the level of the XbaI site made blunt by treatment with the Klenow fragment of DNA polymerase in order to create the construct −2051/+26hAIWT-CAT. The construct hAITaTaTkCAT which comprises a copy of the site of the TaTa box of the human gene for apo A-I cloned before the thymidine kinase promoter of the herpes simplex virus was obtained according to the protocol described for the construct RORETkCAT using the oligonucleotides hAIF1 and hAIR1 (Table 1). In order to exchange the CAT reporter gene of the constructs which comprise fragments of the promoter of the human gene for apo C-III cloned upstream of the CAT reporter gene with the reporter gene Luc+, the luciferase reporter gene Luc+ of the reporter vector pGL3 (Promega) was excised with the enzymes SacI and BamHI and subcloned into the corresponding sites of the vector pBKCMV (stratagene) in order to form the vector pBKCMV-Luc+. The CAT reporter gene of the constructs −1415/+24hCIIIWT-CAT and −1415/+24hCIIIC3P5'KO-CAT was excised with the enzymes KpnI and BamHI. Next, it was replaced with the Luc+ reporter gene obtained by digestion of the plasmid pBKCMV-Luc+ with the enzymes BglII and KpnI in order to create the plasmids −1415/+24hCIIIWT-Luc+ and −1415/+24hCIIIC3P5'KO-Luc+. The point mutants of the apo C-III promoter −1415/+24hCIIIC3P3'KO-Luc+, −1415/+24hCIIIC3P5'+3'KO-Luc+, −1415/+24hCIIITaTaKO-Luc+, −1415/+24hCIIITaTa+C3P5'KO-Luc+, −1415/+24hCIII−TaTa+C3P3'KO-Luc+ were obtained with the aid of the "Quick Change Site Directed Mutagenesis" kit (stratagene) according to the manufacturer's recommendations using the oligonucleotides hC3F20/hC3R20, hC3F30/hC3R30 and hC3F29/hC3R29 (Table 1), respectively. The plasmid Tk-Luc+was constructed by inserting the Luc+ reporter gene obtained by digesting the plasmid pBKCMV-Luc+ with the enzymes BglII and KpnI into the vector pBLCAT4 (29) cut with BglII and KpnI in place of the CAT reporter gene. The constructs $(RevDR2)_{3x}$TkLuc+ and $(RevDR2M3')_{3x}$TkLuc+ were obtained by exchanging the CAT reporter gene of the corresponding constructs with the Luc+ reporter gene (BglII/EcoRI digestion). The corresponding CAT constructs were obtained by the strategy previously described (59) using the oligonucleotides 1129/1142 and 1126/1132 (Table 1). The plasmid −1415/+24hCIIIWT-Luc+was digested with HindIII in order to excise the apo C-III promoter. The DNA fragment obtained was then inserted into the HindIII site of the plasmids pGL3 (Promega) and pSL301 (Pharmacia) in order to create the constructs −1415/+24hCIIIWTpGL3 and −1415/+24hCIIIWTpSL301. The orientation of the insert was then defined. The construct −198/+24hCIIIWTpGL3 was obtained by digesting the construct −1415/+24hCIIIpGL3 with PstI and religation. The construct −1415/+24hCIIIWTpSL301 was then partially digested with the enzyme EcoO109I and self-religated in order to create the construct −108/+24hCIIIWTpSL301. The fragment −108/+24 of the apo C-III promoter was then cloned into the XmaI and HindIII sites of the vector pGL3 in order to create the construct −108/+24hCIIIWTpGL3. In order to create the construct −62/+24hCIIIWTpGL3, the construct −1415/+24hCIIIWTpSL301 was exhaustively digested with the enzyme EcoO109I, made blunt by treatment with the Klenow fragment of DNA polymerase and self-religated. The fragment −62/+24 of the apo C-III promoter was then cloned into the XmaI and HindIII sites of the vector pGL3. The plasmid pTk-pGL3 was constructed by amplifying, by PCR, the fragment of the thymidine kinase promoter of the herpes simplex virus present in the plasmid pBLCAT4 with the aid of the primers 514 and 510 (Table 1), by digesting the PCR fragment obtained with the enzymes BglII and HindIII and by inserting it into the corresponding sites of the vector pGL3. The constructs $(-27/-58)_{3x}$hCIIITkpGL3, $(-58/-27)_{8x}$hCIIITkpGL3 and $(-47/-79)$hCIIITkpGL3 were obtained according to the strategy described above (Vu Dac et al., JCI, 96, 741–750, 1995) with the aid of the oligonucleotides hC3F15/hC3R15 and hC3F17/hC3R17, respectively. The intermediate constructs in the vector pic20H were digested with the enzymes SalI and XhoI. The inserts obtained were then cloned into the XhoI site of the vector TkpGL3 and their orientation defined by sequence. The oligonucleotides hC3F18 and hC3R18 were used as primers in order to create, by PCR with the aid of the Pfu polymerase (stratagene), a DNA fragment which contains several copies of the −30/−15 fragment of the apo C-III promoter. This fragment was digested with the enzymes XhoI and SpeI and inserted into the vector TkpGL3 previously cut with the enzymes NheI and XhoI in order to create the construct $(-30/-1)_n$TkpGL3. The oligonucleotides hC3F22 and hC3R22 were used as primers to create, by PCR with the aid of the Pfu polymerase (stratagene), a DNA fragment which contains several copies of the −103/−73 fragment of the apo C-III promoter. This fragment was digested with the enzymes XhoI and SpeI and inserted into the vector TkpGL3 previously cut with the enzymes NheI and XhoI in order to create the construct $(-76/-100)_{2x}$TkpGL3. The plasmid pG5TkpGL3 was obtained by inserting 5 copies of the response element of the yeast transcription factor Gal4 (site 17 m) (46) upstream of the Tk promoter into the plasmid TkpGL3.

The plasmids pCMX-hRORα1, pCMX-hRORα2, pCMX-hRORα3 allowing the exogenous expression of the corresponding nuclear receptors have been obtained and described before (47). The plasmid pCDNA3-hRORα1 was constructed by restricting the plasmid pCMX-hRORα1 with the aid of the enzymes KpnI and partially with XbaI and cloning the insert into the corresponding sites of the vector pCDNA3. To generate the plasmid pSG5-hRORα1, the plasmid pCMX-hRORα1 was digested with the enzyme KpnI, made blunt by treatment with the Klenow fragment of DNA polymerase and digested with BamHI. The insert obtained was cloned into the vector pSG5 digested with EcoRI, made blunt by treatment with the Klenow fragment of DNA polymerase and digested with BamHI. The plasmid pGal4-φ was constructed by subcloning the DNA binding domain of the yeast transcription factor Gal4 present in the plasmid pBD-Gal4 (stratagene) into the HindIII-EcoRI sites of the vector pCDNA3. To generate the plasmid pBDGal4-hRORαDEF, the plasmid pSG5-hRORα1 was cut with the enzyme XhoI, made blunt by treatment with the Klenow fragment of DNA polymerase and digested with XmaI. This insert was then cloned into the vector pBDGal4 previously restricted with EcoRI, made blunt by treatment with the Klenow fragment of DNA polymerase and digested with XmaI. The plasmid pBDGal4-hRORαDEF was then digested with the enzymes HindIII and EcoRI. The insert obtained was cloned into the corresponding sites of the vector pCDNA3 in order to create the plasmid pGal4-hRORαDEF.

All the constructs were checked by sequencing.

3. Transient transfection and measurement of the promoter activity of human apo C-II The activity of the nuclear receptors was measured by conventional reporter gene/cotransfection techniques. The DNA was introduced into the cells studied using common technologies available in the laboratory (calcium phosphate, electroporation, lipofection and the like). The vectors pSG5, pCDNA3 and pCMX were used as negative controls. In the experiments carried out with the aid of the calcium phosphate precipitation technique, the cells plated on 60-mm culture plates were transfected at 50–60% confluence with a mixture of plasmids which comprised, in addition to the reporter plasmids CAT, Luc+ or pGL3 (0.5 μg/60-mm plate) and the expression vectors pSG5-hRORα1, pCMX-hRORα1, pCMX-hRORα2 and pCMX-hRORα3 (0.1–1 μg/60-mm plate), 0.1 μg/60-mm plate of plasmid pCMV-β-gal (Clontech) used as control for transfection efficiency (30). After 5 to 6 hours, the cells were washed twice with the aid of a wash buffer (0.15 M NaCl, 0.01 M sodium phosphate, pH 7.2) and incubated for 36 hours in fresh culture medium containing 10% foetal calf serum. After the transfection, the cells were lysed and the luciferase and β-galactosidase activities were measured according to conventional protocols (31). For the experiments carried out by lipofection, the cells were plated on 24-well plates in an amount of 10,000 cells per well and incubated for 16 hours at 37° C. before transfection. The cells were then transfected for two hours at 37° C. in a serum-free culture medium with the aid of a cationic lipid. The plasmids (reporter vectors: 50 ng/well; expression vectors: 100 ng/well, vectors for control of transfection efficiency: pSV-βgal (Promega) (50 ng/well) and carrier DNA (pBluescript (stratagene) added to take the quantity of transfected DNA to 500 ng/well) were dissolved in serum-free DMEM supplemented with NaCl (150 mM), sodium bicarbonate (50 mM) and cationic lipid (6 nmol/μg DNA), vortexed, incubated for 30 minutes at room temperature and added to the cells. After incubating for two hours, the cells were rinsed with the aid of the wash buffer described above and incubated for 36 hours in fresh culture medium containing 10% foetal calf serum. At the end of the experiment, the cells were rinsed with the aid of the wash buffer and the luciferase activity measured with the aid of the "Dual-Luciferase Reporter Assay System" kit from Promega according to the manufacturer's instructions. The protein content of the extracts obtained was assayed by the Bradford technique with the aid of the "Bio-Rad Protein Assay" kit (Bio-Rad).

4. Gel Retardation

The hRoRα1 protein was synthesized in vitro starting with the plasmid pCMX-hRoRα1 by the reticulocyte lysate technique with the aid of the "TnT T7 quick coupled transcription/translation system" kit from Promega. The gel retardation experiments were carried out according to the protocol described before (48 and 49) using double-stranded oligonucleotides phosphorylated at the ends using polynucleotide kinase in the presence of [γ-$^{32}$P]ATP. 500 picomol of oligonucleotides 82 and 512 were labelled with the aid of polynucleotide kinase and [γ-$^{32}$P]ATP, purified on a silica matrix (Quiagen) according to the manufacturer's protocol and used as primers to amplify the −198/+24 fragment of the apo C-III promoter using the plasmid −198/+24hCIIIWT-Luc+ as template. The PCR fragment obtained was then purified on a silica matrix (Quiagen) according to the manufacturer's instructions and used as probe.

The identity of the oligonucleotides used to synthesize the double-stranded DNAs used as probes is described in Table 2.

The double-stranded oligonucleotides were obtained by incubating 2.5 or 5 μg of sense and anti-sense oligonucleotides diluted in hybridization buffer (50 mM Tris-HCl pH 8, 50 mM KCl, 5 mM MgCl$_2$, 10 mM DTT) at 100° C. for 10 min and then at 65° C. for 10 min and slowly cooling the mixture to room temperature. They were phosphorylated at the 5' ends using polynucleotide kinase in the presence of [γ-$^{32}$P]ATP as described before (48 and 49).

The binding buffer had the following composition: 10 mM Hepes, 50 mM KCl, 1% glycerol, 2.5 mM MgCl$_2$, 1.25 mM DTT, 0.1 μg/μl polydIdC, 50 ng/μl herring sperm DNA, 1 μg/μl bovine serum albumin, 10% reticulocyte lysate.

During the competition experiments, increasing concentrations of nonlabelled double-stranded oligo-nucleotides (molar excess of 10 to 100 fold) were added to the mixtures and incubated for 15 min at room temperature before the addition of the radioactive probes. After addition of the radioactive probes, the reticulocyte lysates were added to the mixture and incubated for 15 min at room temperature before the separation of the protein/DNA complexes by electrophoresis on a polyacrylamide gel (4%) in a 0.25× Tris-borate-EDTA buffer at room temperature (50).

5. Mice

The staggerer homozygotes mutant mice (sg/sg) developes, compared with the wild type C57BL/6 SG/+SG, cerebral ataxia and neurodegeneration (23, 24) as well as immunity abnormalities, such as hyperproduction of inflammatory cytokines (26, 25). The sg/sg mice carry a deletion in the RORα gene. This deletion prevents the translation of the putative ligand binding domain, thereby disrupting the functioning of this transcription factor (27). The staggerer mutation being maintained in the C57BL/6 genome which allows analysis of the development of atherosclerotic lesions after subjecting to an atherogenic region, the plasma lipoprotein and apolipoprotein profiles, the extent of fat plaques in the aorta and the incidence of atherosclerosis in the coronary arteries were determined by subjecting sg/sg mice to an atherogenic regime rich in fat and by comparing them with +/+C57BL/6 mice. The results showed that the sg/sg mice develop severe atherosclerosis, which suggests the important role of RORα in cardiovascular diseases.

The male and female C57BL/6 mice (6 to 8 weeks old) were obtained from CERJ (France), the staggerer mutant mice (sg/sg) were obtained by crossing known heterozygotes (+/sg) and identifying the homozygous progeny by their ataxia. The sg mutation was developed on a C57BL/6 genetic background.

6. Analysis of the RNAs

The mice are sacrificed with an ether overdose. The RNA extractions, the "northern" and "dot blot" hybridizations, the measurements of the levels of messenger RNA for apo C-III are carried out as described before (32). The 36B4 cDNA clone (33) encoding human acidic ribosomal phosphoprotein PO (34) is used as control. The cDNA probes are labelled using random hexamers as primer (Boehringer Mannheim). The filters are hybridized with $1.5 \times 10^6$ cpm/ml of each probe as described (35). They are washed once in 0.5×SSC and 0.1% SDS for 10 minutes at room temperature and twice for 30 minutes at 65° C. and then subsequently exposed to an X-ray film (X-OMAT-AR, Kodak). The autoradiograms are analysed by quantitative scanning densitometry (Biorad GS670 densitometer) and the results are normalized relative to the 36B4 messenger RNA levels (35).

II. FIGURES

FIG. 1: Stimulation of the activity of the promoter of the human apo C-III gene with hRORα1 in HepG2 cells.

Figure 2:
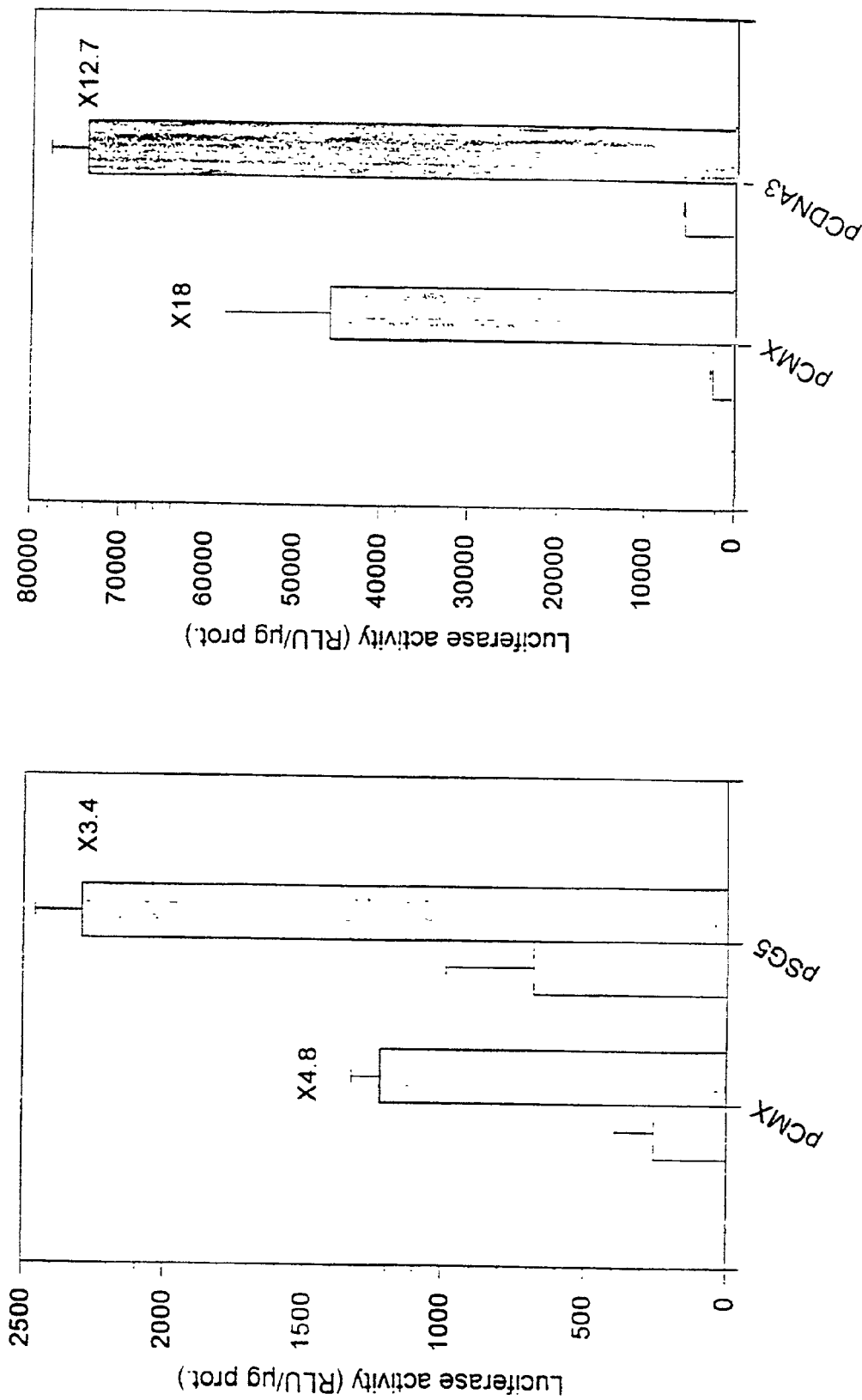

FIG. 2: Activation of the apo C-III promoter with hRORα1: comparison of three expression vectors and of two transfection methods.

Figure 3:
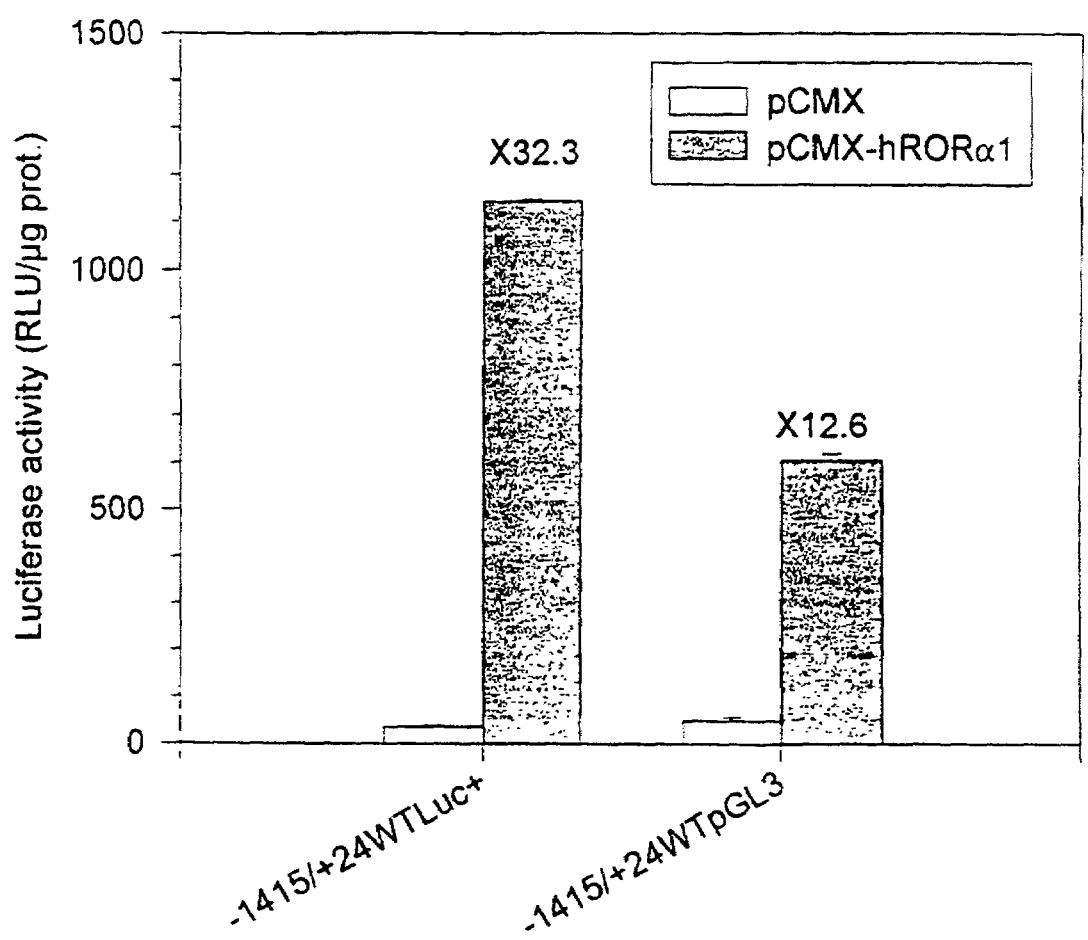

FIG. 3: Comparison of the stimulation of the activity of the apo C-III promoter cloned into two different reporter vectors.

Figure 4:
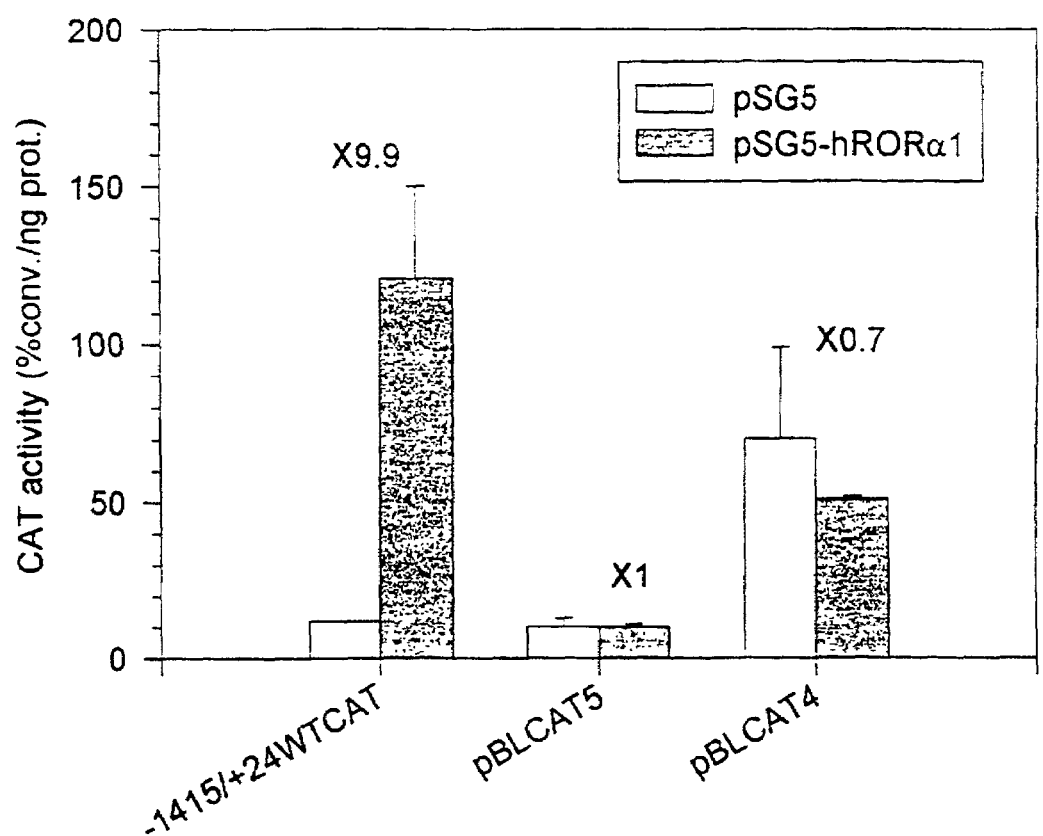

FIG. 4: Stimulation of the activity of the promoter of the human apo C-III gene cloned into the vector pBLCAT5 with hRORα1 in RK13 cells.

Figure 5:
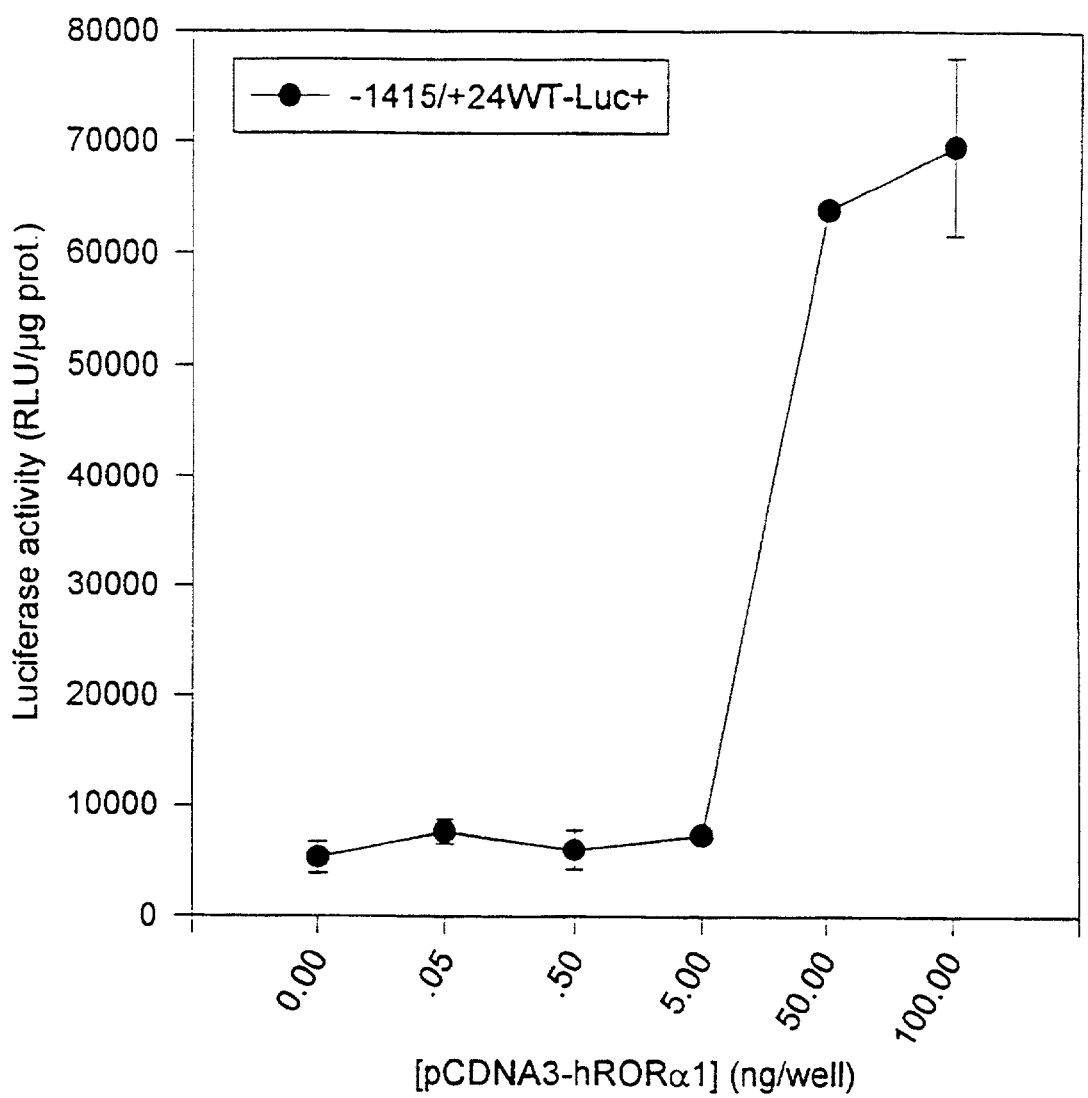

FIG. 5: Stimulation of the activity of the construct −1415/+24hCIIIWT-Luc+ with increasing quantities of plasmid pCDNA3-hRORα1 cotransfected into RK13 cells.

Figure 6:
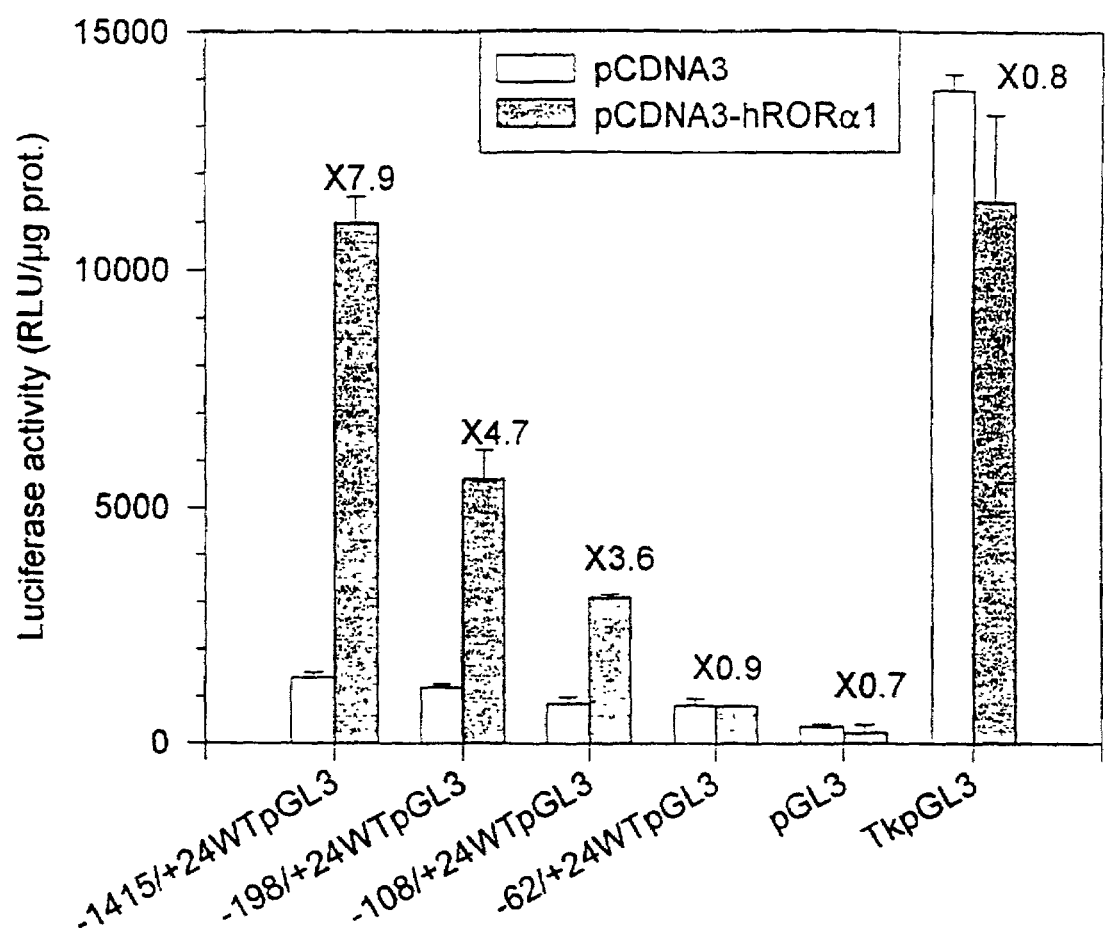

FIG. 6: Stimulation of the activity of fragments of decreasing size of the promoter of the human apo C-III gene cloned into the vector pGL3 with hRORα1 in RK13 cells.

Figure 7:
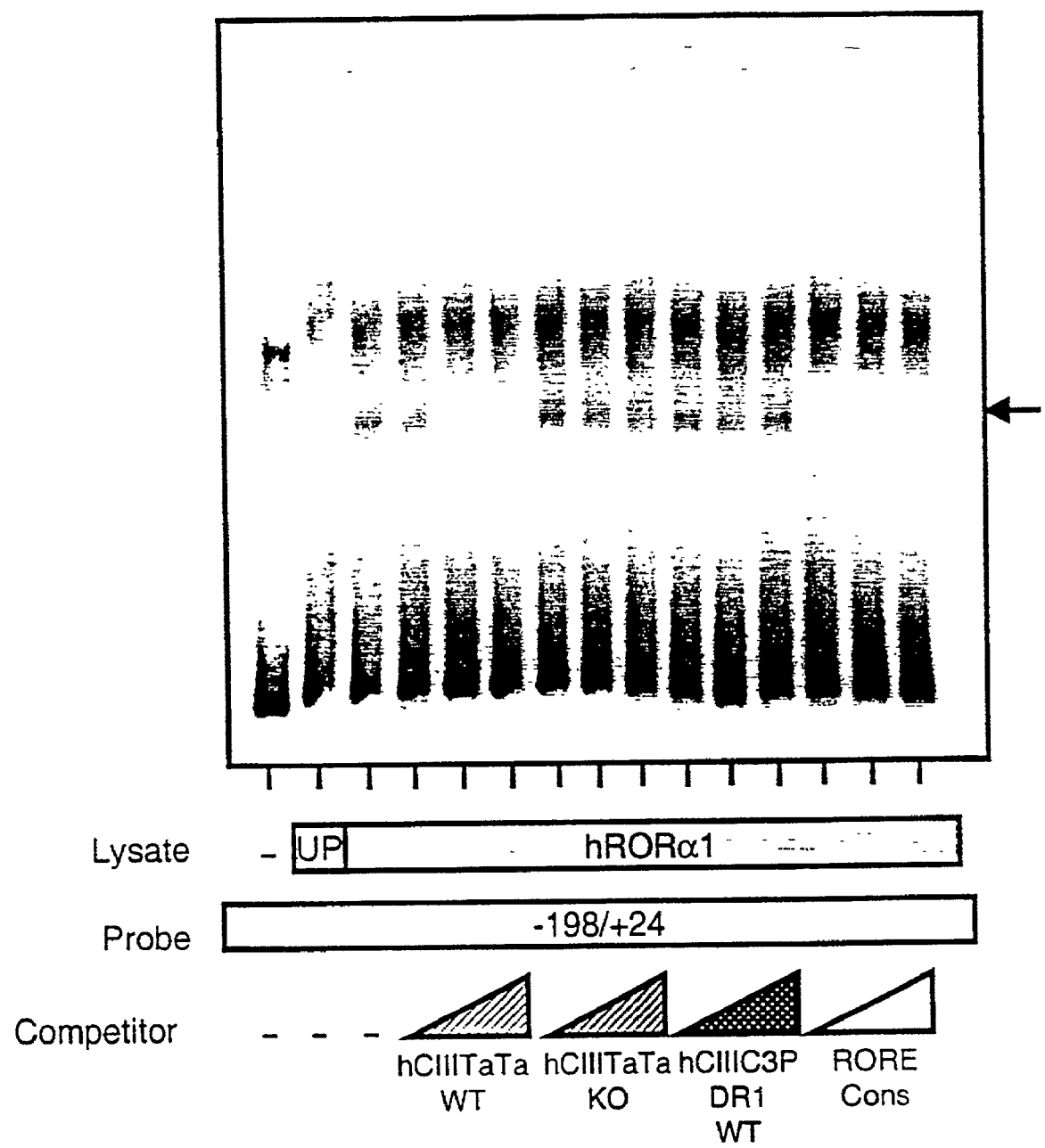

FIG. 7: Evaluation of the binding of hRORα1 to the proximal promoter of the human gene for apo C-III by gel retardation.

Figure 8:
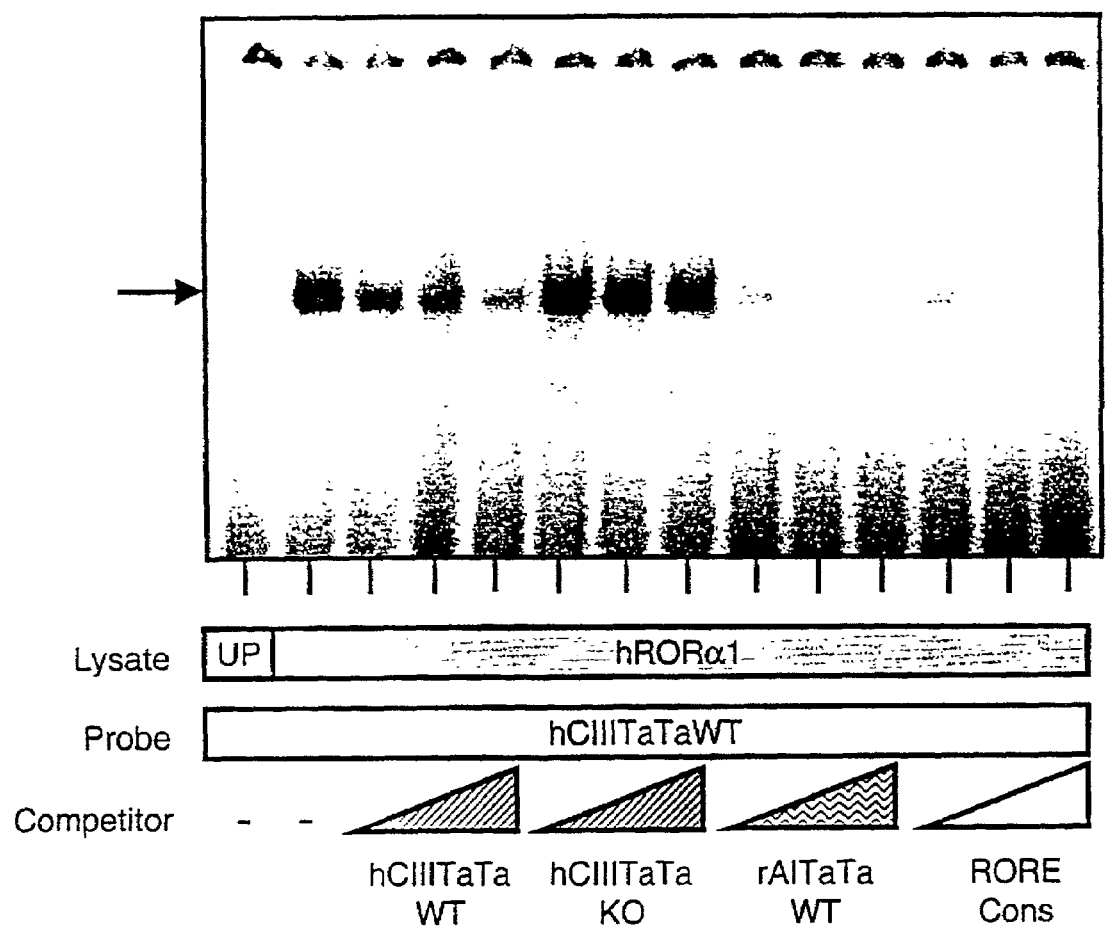

FIG. 8: Evaluation of the binding of hRORα1 to the −34/−10 fragment of the promoter of the human gene for apo C-III by gel retardation.

Figure 9:
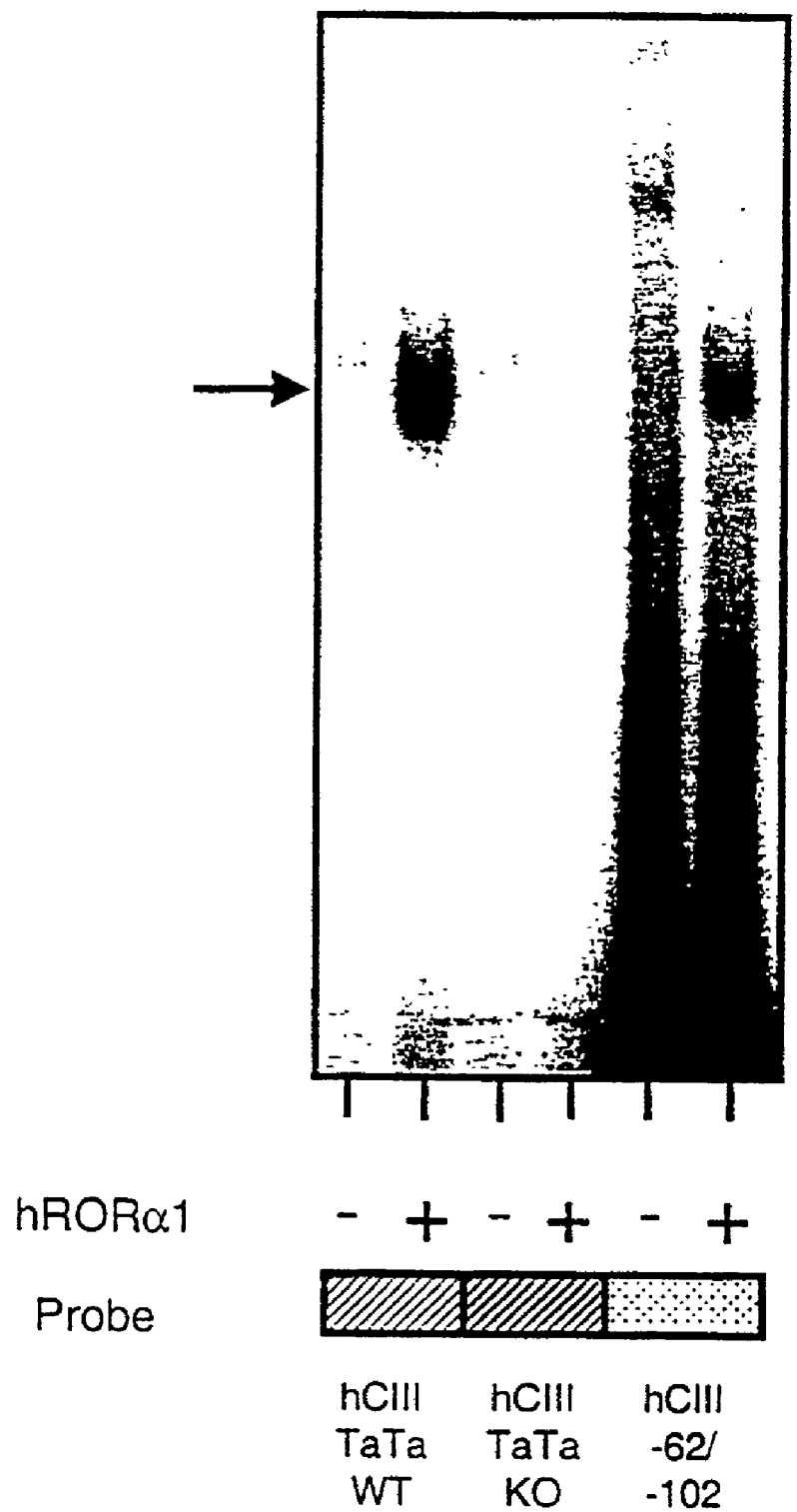

FIG. 9: Evaluation of the binding of hRORα1 to the −34/−10 and −62/−100 fragments of the promoter of the human gene for apo C-III by gel retardation.

Figure 10:
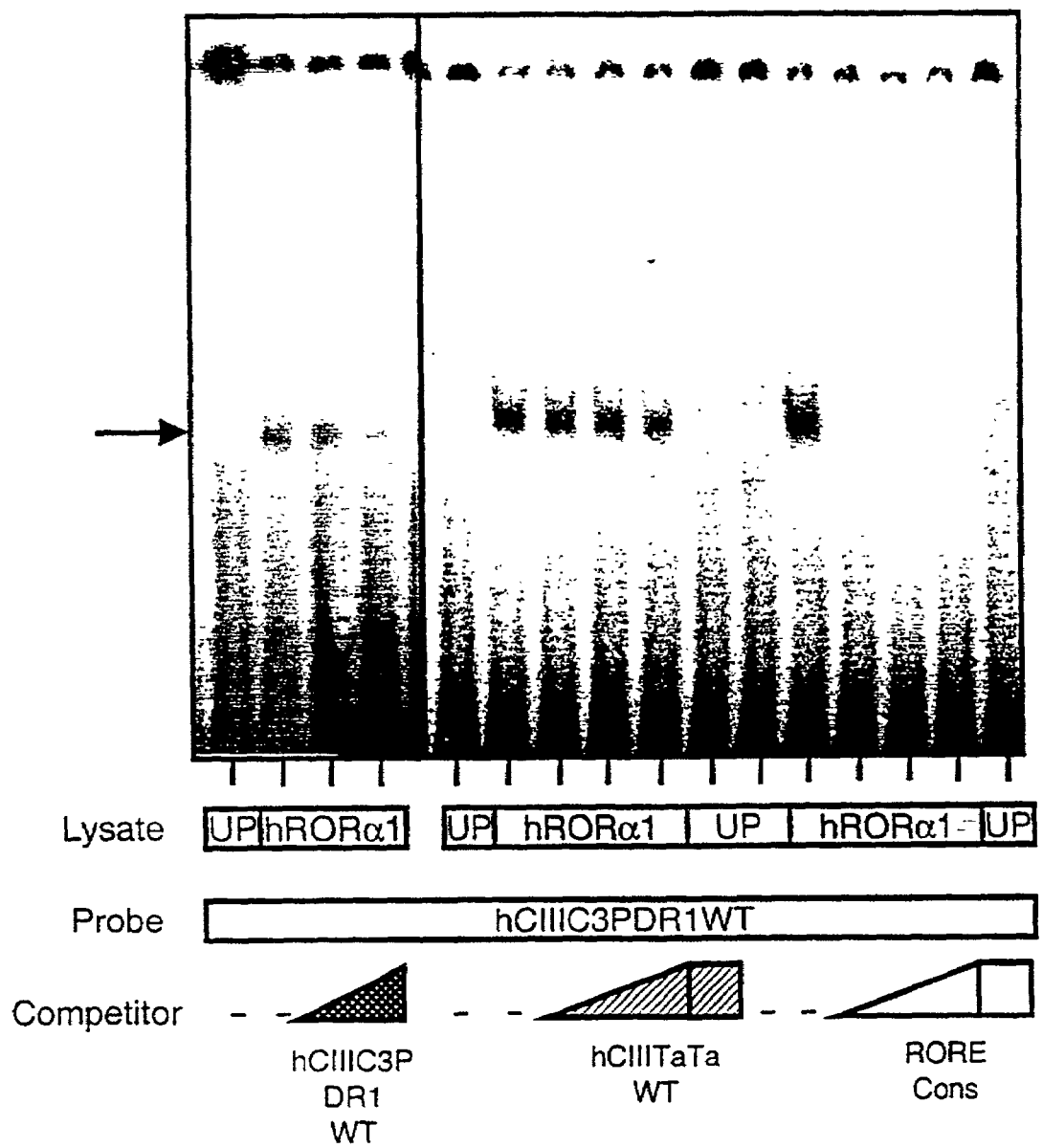

FIG. 10: Evaluation of the binding of hRORα1 to the −90/−64 fragment of the promoter of the human gene for apo C-III by gel retardation.

Figure 11:
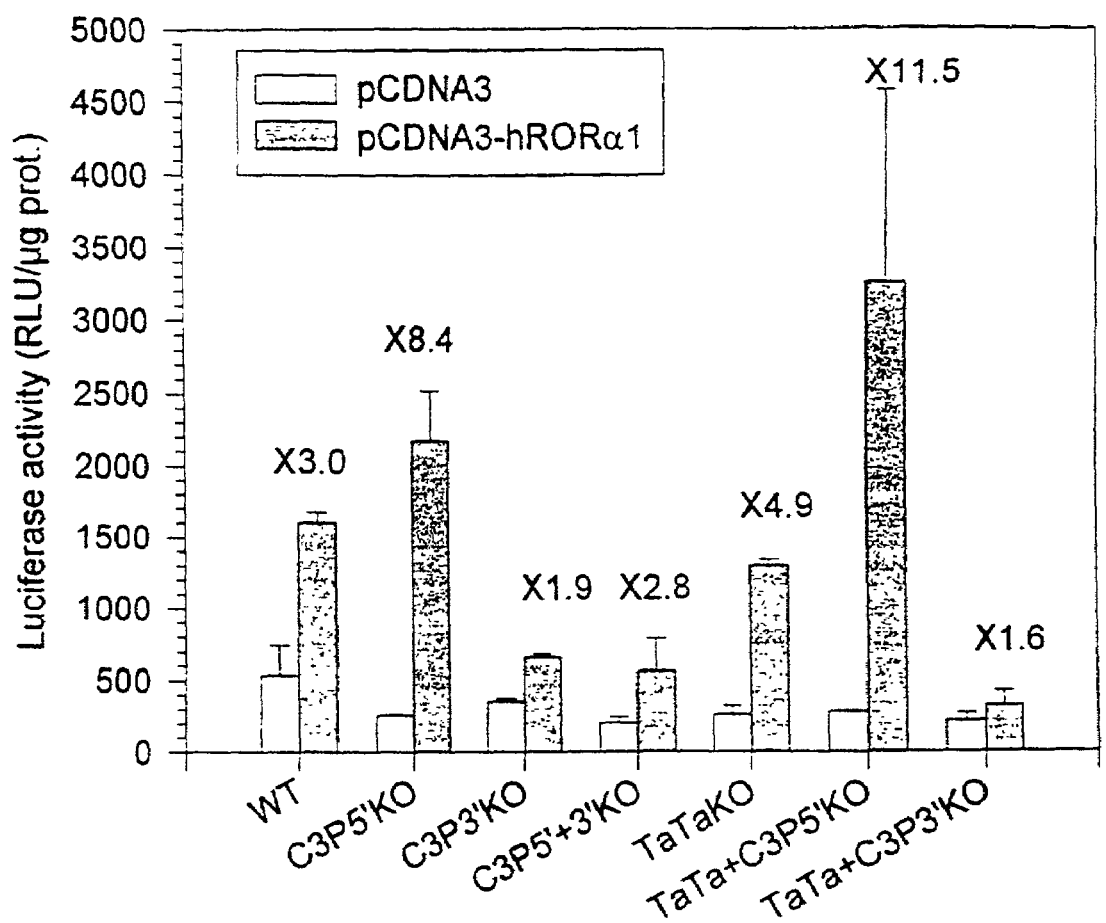

FIG. 11: Stimulation of the activity of point mutants of the promoter of the human apo C-III gene with hRORα1 in RK13 cells.

Figure 12:
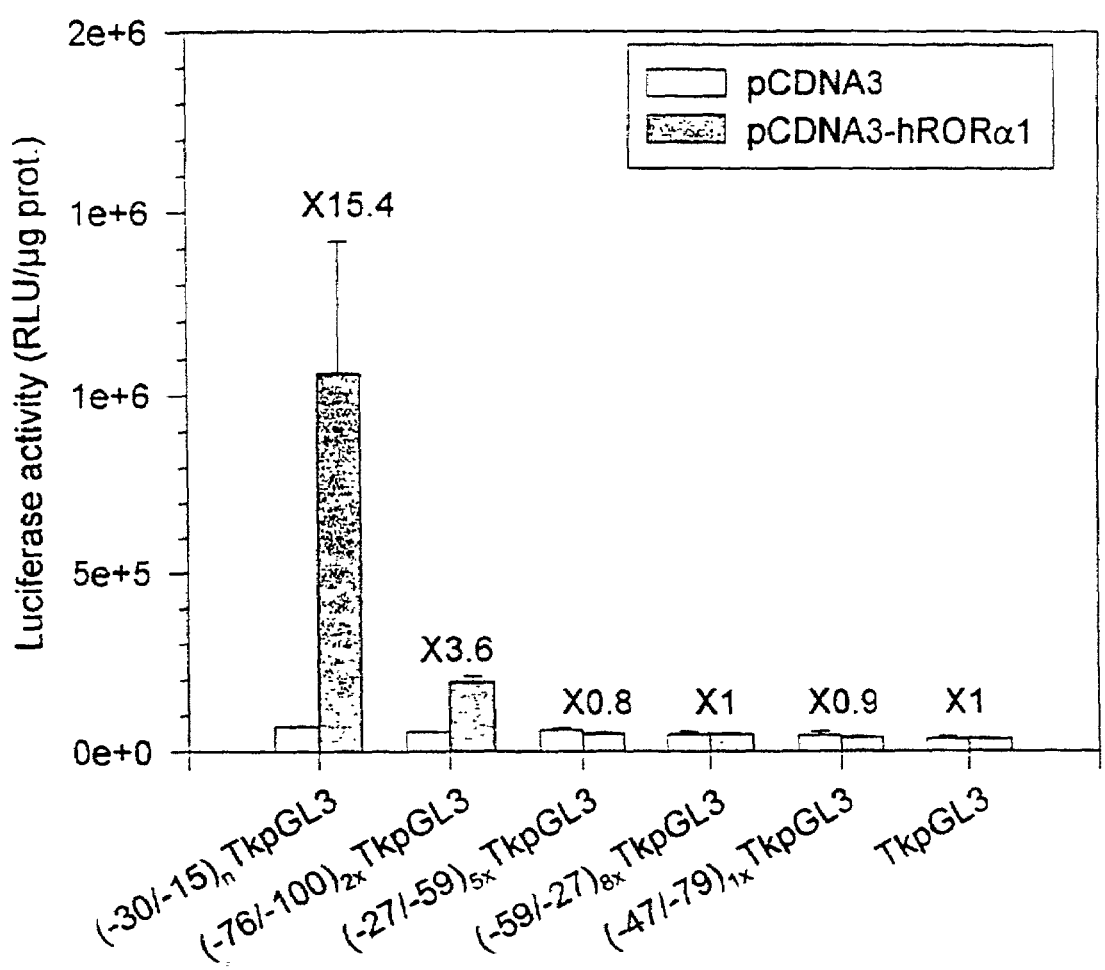

FIG. 12: Stimulation of the activity of fragments of the promoter of the human apo C-III gene cloned before the thymidine kinase promoter of the herpes simplex virus with hRORα1 in RK13 cells.

FIG. 13: Novelty of the activation with hRORα1 of the promoter of human apo C-III.

Figure 14:
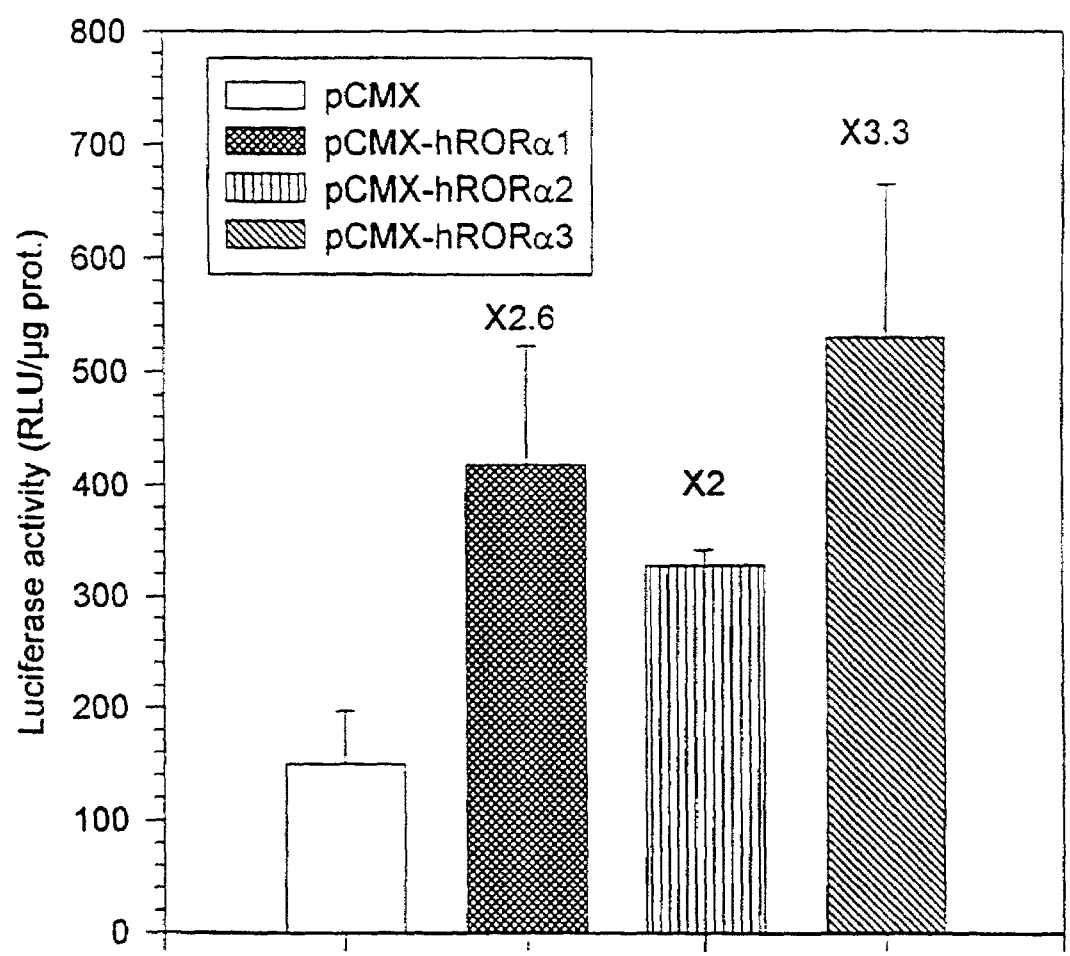

FIG. 14: Stimulation of the activity of the promoter of the human apo C-III gene with the α1, α2 and α3 isoforms of hRORα in RK13 cells.

Figure 15:
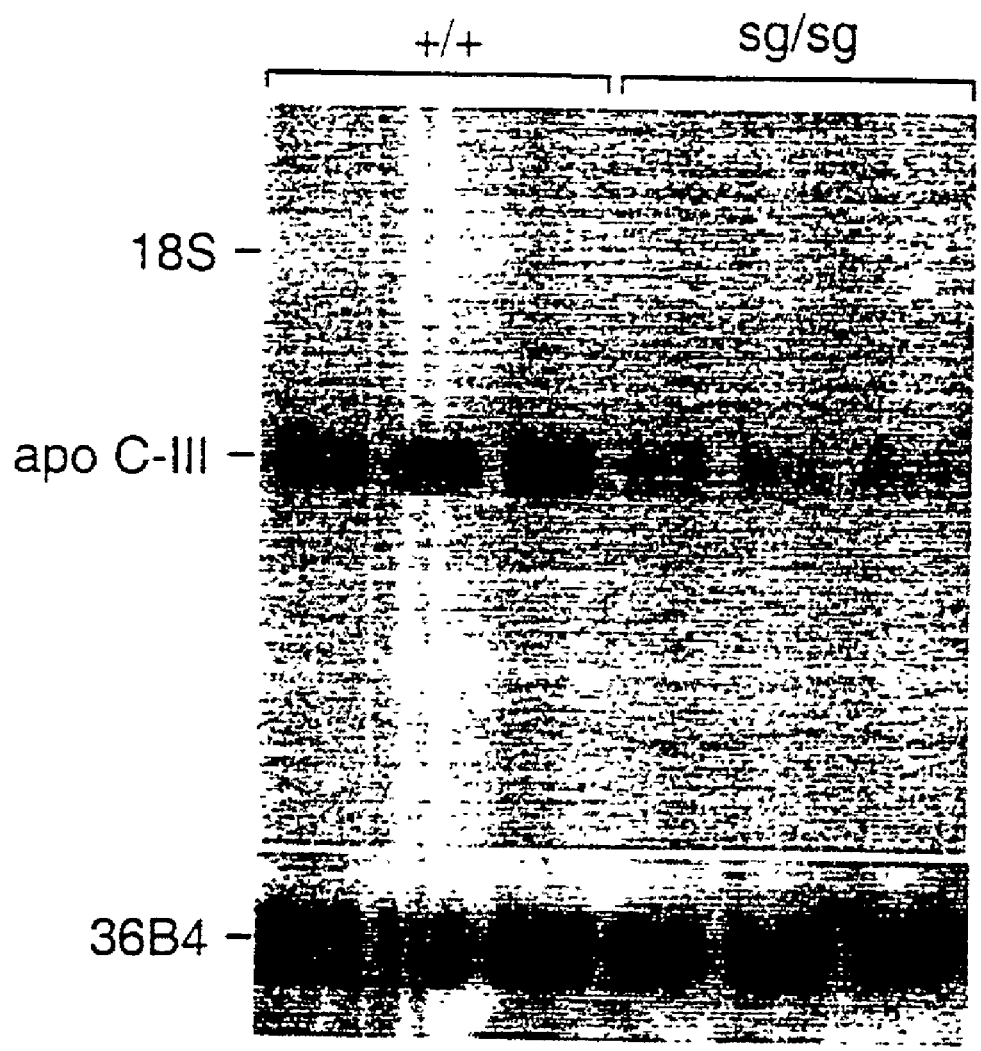

FIG. 15: Hepatic expression of the apo C-III gene in sg/sg mutant or SG/SG wild-type mice.

Figure 16:
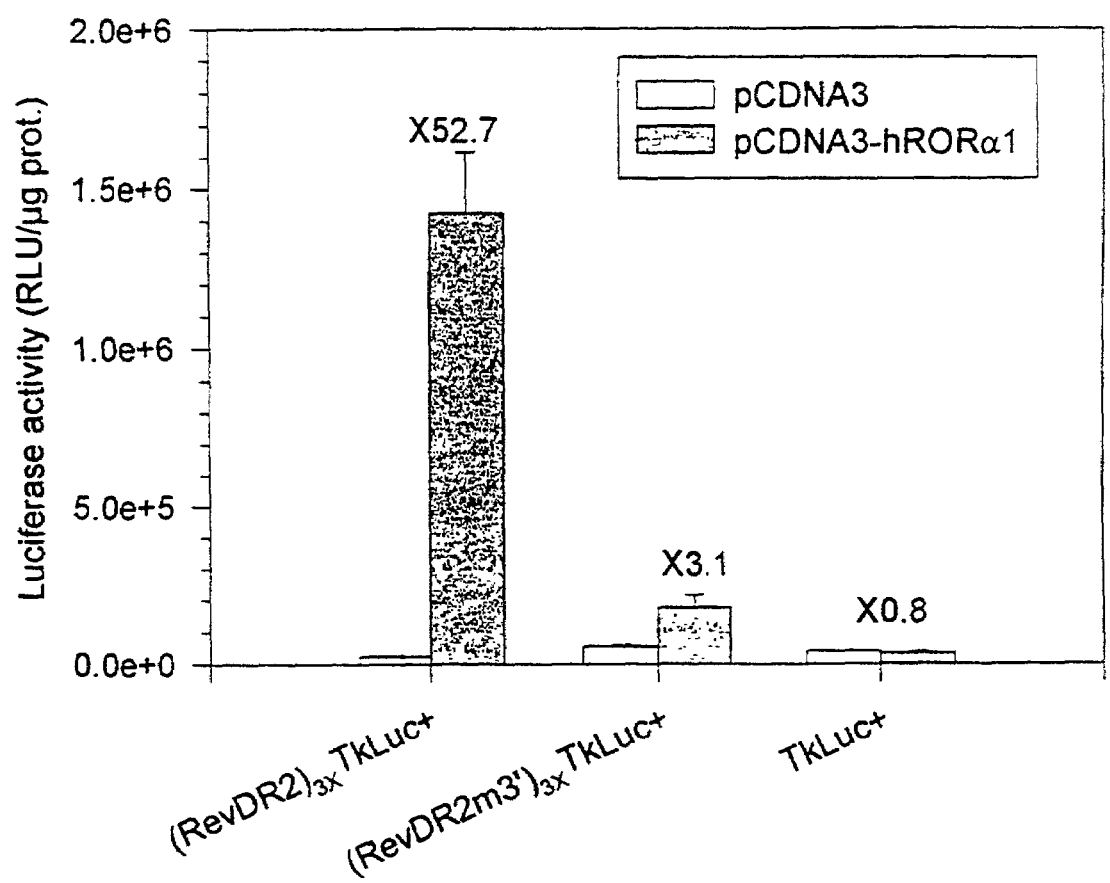

FIG. 16: Validation of a reporter vector appropriate for the screenings of substances capable of modulating the activity of hRORα.

Figure 17:
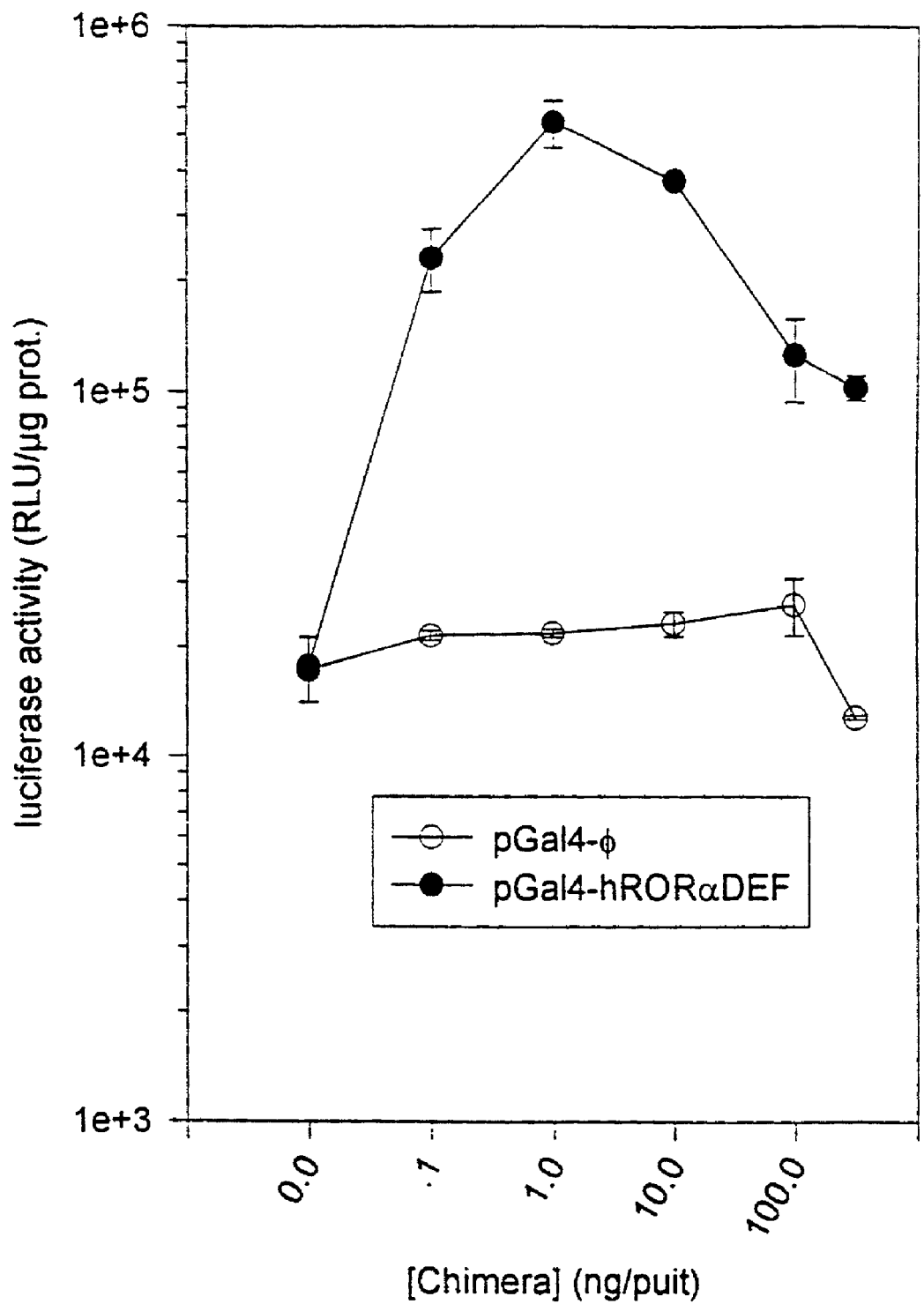

FIG. 17: Validation of a screening test for substances capable of modulating the activity of hRORα based on the use of a chimera which combines the DNA binding domain of the yeast transcription factor Gal4 and the ligand binding domains DEF of hRORα.

III. RESULTS 1. hRORα Activates the Human apo C-III Promoter in HepG2 Cells

FIG. 1 illustrates the sensitivity of the promoter of the human gene for apo C-III to the exogenous expression of the nuclear receptor hRORα1 induced in HepG2 cells.

In this figure, the HepG2 cells were plated on 60-mm culture plates and transfected at 50–60% confluence by the calcium phosphate technique with 500 ng/plate of reporter vector −1415/+24hCIIIWT-Luc+, 1 µg/plate of expression vector pCMX (negative control) or pCMX-hRORα1 as indicated and 100 ng/plate of the plasmid pCMV-βgal used as control for transfection efficiency. After incubating for 36 hours, the cells were rinsed, lysed and the luciferase and β-galactosidase activity of the cellular extracts measured according to conventional protocols (31).

These cells were cotransfected with a reporter plasmid containing the part of the promoter of the apo C-III gene between positions −1415 and +24 cloned upstream of the luciferase reporter gene (−1415/+24hCIIIWT-Luc+) and the expression vector pCMX-hRORα1. This observation suggests the presence of an hRORα1 nuclear receptor response element in the −1415/+24 portion of the promoter of human apo C-III.

2. hROR Activates the Human apo C-III Promoter in RK13 Cells

In order to determine if the activation of the human apo C-III promoter with hRORα1 depends on the cellular context and in order to identify a more stable experimental model than HepG2 cells, the experiment was repeated on RK13 cells. Similar results are obtained (FIG. 2).

In experiment 1, the RK13 cells were plated on 60-mm culture plates and transfected at 50–60% confluence by the calcium phosphate technique with 500 ng/plate of reporter vector −1415/+24hCIIIWT-Luc+, 1 µg/plate of expression vector pCMX or pSG5 (negative controls) or pCMX-hRORα1 or pSG5-hRORα1 as indicated and 100 ng/plate of the plasmid pCMX-βgal used as control for transfection efficiency. After incubating for 36 hours, the cells were rinsed, lysed and the luciferase and β-galactosidase activity of the cellular extracts measured according to conventional protocols (31). In experiment 2, 10,000 RK13 cells were plated per well of a 24-well culture plate and transfected with the aid of a cationic lipid with 50 ng/well of reporter vector −1414/+24hCIIIWT-Luc+, 100 ng/well of expression vector pCMX or pCDNA3 or pCMX-hRORα1 or pCDNA3-hRORα1 as indicated and 50 ng of vector pSV-βgal. The total quantity of transfected DNA was brought to 500 ng/well with the aid of the plasmid pBluescript used as carrier. After incubating 36 hours, the cells were rinsed, lysed and the luciferase activity of the cellular extracts assayed with the aid of the "Dual-Luciferase™ Reporter Assay System" kit from Promega. The β-galactosidase activity of the cellular extracts was measured according to the conventional protocol (31).

This model, whose phenotype is more constant than that of the HepG2 cells will therefore be subsequently used for the characterization of the effect of hROR and of its isoforms.

3. The effect of hRORα1 is independent of the Mode of Transfection, the Expression Vector and the Reporter Gene Used The activation of the construct −1415/+24hCIIIWT-Luc+ with pCMX-hRORα1 is observed regardless of the transfection protocol used, precipitation of DNA with calcium phosphate or lipofection (FIG. 2). Since the transfection efficiency by the second method is higher, since the quantities of DNA used may be substantially reduced and since the transfection may be carried out in the presence of an excess of inert carrier DNA, the latter method is preferred. The activation of the construct −1415/+24hCIIIWT-Luc+ with hRORα1 is observed with the vectors pCMX-hRORα1, pSG5-hRORα1 and pCDNA3-hRORα1 (FIG. 2). Since the exogenous expression of hRORα1 induced by the vector pCDNA3-hRORα1 appears to be more efficient (data not illustrated) and since the empty vector pCDNA3 interferes little with the basic activity of the construct −1415/+24hCIIIWT-Luc+, this vector is preferably used. The activation of the portion between positions −1415 and +24 of the apo C-III promoter is observed when it is cloned before the Luc+ reporter gene into the vector Luc+ or into the vector pGL3 (Promega) (FIG. 3) as well as before the CAT reporter gene into the vector pBLCAT5 (FIG. 4).

In FIG. 3, 10,000 RK13 cells were plated per well of a 24-well culture plate and transfected with the aid of a cationic lipid with 50 ng/well of reporter vector −1415/+24HCIIIWT-Luc+(noted −1415/+24WTLuc+) or −1415/+24hCIIIWTpGL3 (noted −1415/+24hWTpGL3) as indicated, 100 ng/well of expression vector pCDNA3 or pCDNA-hRORα1 as indicated and 50 ng of vector pSV-βgal. The total quantity of transfected DNA was brought to 500 ng/well with the aid of the plasmid pBluescript used as carrier. After incubating for 36 hours, the cells were rinsed, lysed and the luciferase activity of the cellular extracts assayed with the aid of the "Dual-Luciferase™ Reporter Assay System" kit from Promega. The β-galactosidase activity of the cellular extracts was measured according to the conventional protocol (31).

In FIG. 4, the RK13 cells were plated on 60-mm culture plates and transfected at 50–60% confluence by the calcium phosphate technique with 500 ng/plate of reporter vector −1415/+24hCIIIWT-CAT (noted −1415/+24WTCAT), pBLCAT5 or pBLCAT4 (30), as indicated, 1 µg/plate of expression vector pSG5 (negative control) or pSG5-hRORα1 as indicated and 100 ng/plate of plasmid pCMV-βgal used as control for transfection efficiency. After incubating for 36 hours, the cells were rinsed, lysed and the CAT and β-galactosidase activity of the cellular extracts measured according to conventional protocols (31).

In conclusion, the activation with hRORα1 of the portion between positions −1415 and +24 of the apo C-III promoter is observable in all the experimental systems tested: the effect is robust.

4. The effect of hRORα1 Depends on the Quantity of Expression Vector Transfected FIG. 5 illustrates the dependence of the effect of hRORα1 on the activity of the construct −1415/+24hCIIIWT-Luc+ in relation to the quantity of expression vector transfected.

In FIG. 5, 10,000 RK13 cells were plated per well of a 24-well culture plate and transfected with the aid of a cationic lipid with 50 ng/well of reporter vector −1415/+24hCIIIWT-Luc+(noted −1415/+24WTLuc+), from 0 to 100 ng/well of expression vector pCDNA3-hRORα1 (supplemented with the plasmid pCDNA3 in order to maintain the number of transcriptional units constant) as indicated and 50 ng of vector pSV-βgal. The total quantity of transfected DNA was brought to 500 ng/well with the aid of the plasmid pBluescript used as carrier. After incubating 36 hours, the cells were rinsed, lysed and the luciferase activity of the cellular extracts assayed with the aid of the "Dual-Luciferase™ Reporter Assay System" kit from Promega. The β-galactosidase activity of the cellular extracts was measured according to the conventional protocol (31).

5. The effect of hRORα1 is Specific

In FIG. 6, 10,000 RK13 cells were plated per well of a 24-well culture plate and transfected with the aid of a cationic lipid with 50 ng/well of reporter vectors −1415/+24hCIIIWTpGL3 (noted −1415/+24WTpGL3), −198/+24hCIIIWTpGL3 (noted −198/+24WTpGL3), −108/+24hCIIIWTpGL3 (noted −108/+24WTpGL3), −62/+24hCIIIWTpGL3 (noted −62/+24WTpGL3), pGL3 and TkpGL3 (negative controls) as indicated, 100 ng/well of expression vector pCDNA3 or pCDNA3-hRORα1 as indicated and 50 ng of vector pSV-βgal. The total quantity of transfected DNA was brought to 500 ng/well with the aid of the plasmid pBluescript used as carrier. After incubating for 36 hours, the cells were rinsed, lysed and the luciferase activity of the cellular extracts assayed with the aid of the "Dual-Luciferase™ Reporter Assay System" kit from Promega. The β-galactosidase activity of the cellular extracts was measured according to the conventional protocol (31).

FIGS. 4 and 6 indicate that the activity of the reporter gene of the promoter-free vectors (pBLCAT5, pGL3), into which the fragment between positions −1415 and +24 of the apo C-III promoter is cloned is not increased by the exogenous expression of hRORα1. Furthermore, the activity of a heterologous promoter, the promoter of the thymidine kinase gene of the herpes simplex virus, is also insensitive to the action of hRORα1. The effect of this nuclear receptor on the promoter of the human gene for apo C-III is therefore specific.

6. Identification of the Molecular Mechanism of action of hRORα1 a. Analysis of the Deletion Mutants of the Promoter

FIG. 6 shows a gradual decrease in the hRORα1 activity when the fragment of the apo C-III promoter cloned upstream of a reporter gene is truncated up to position −108

(construct −108/+24hCIIIWTpGL3). The response to hRORα1 disappears starting from the deletion −62/+24hCIIIWTpGL3. This suggests the presence of sequence elements essential for the activity of hRORα1 between positions −62 and −108. The difference in sensitivity to hRORα1 observed between the constructs −1415/+24hCII-WTpGL3 and −198/+24hCIIIWTpGL3 (FIG. 6) suggests the presence, in the region between positions −1415 and −198, of hRORα1 response elements or of a site of attachment of nuclear factors which act in synergy with hRORα1. The role of such sites in the control of the activity of the apo C-III promoter, for example, by the nuclear factor HNF4 is known in the state of the art (60).

b. Analysis of the Promoter by Gel Retardation

In order to validate in vitro the binding of hRORα1 to the −198/+24 fragment of the apo C-III promoter, it was amplified by PCR with the aid of primers radioactively labelled with $[\gamma\text{-}^{32}P]$ATP and purified. Moreover, the hRORα1 protein was synthesized in vitro from the plasmid pCMX-hRORα1 with the aid of rabbit reticulocyte lysate. The labelled DNA was incubated in the presence of reticulocyte lysate containing the hRORα1 protein or lysate not programmed to express the protein. The DNA/protein complexes thus obtained were then resolved on polyacrylamide gel ("gel retardation" method). A complex specific for hRORα1 on the −198/+24 fragment was identified and is marked with an arrow in FIG. 7.

In FIG. 7, the −198/+24 fragment of the promoter of the human gene for apo C-III was amplified by PCR with the aid of the primers 82 and 512 (Table 1) previously phosphoryiated at the 5' end by poly-nucleotide kinase in the presence of $[\gamma\text{-}^{32}P]$ATP. This probe was incubated in the presence of reticulocyte lysate (TNT-T7, Promega) programmed to express the hRORα1 receptor according to the protocol defined by the manufacturer or in the presence of control lysate. The DNA/protein complexes were then separated on a non denaturing polyacrylamide gel. After drying, the gel is subjected to autoradiography. The first lane of the gel corresponds to the migration of the probe alone. The second lane corresponds to the migration of the probe incubated in the presence of the control lysate. Other lanes correspond to the migration of the probe incubated in the presence of lysate programmed to express hRORα1. A molar excess (10, 50, 100x) of the nonlabelled double-stranded oligonucleotides indicated was preincubated with the programmed lysate for 15 minutes before the addition of the probe.

The formation of this complex is reduced by the addition of nonlabelled double-stranded oligonucleotide (competitors) added in excess whose sequences correspond to the consensus response element of hRORα1 (RORECons) and to the half-site AGGTCA present downstream of the TaTa box of the human apo C-III gene (hCIII-TaTaWT) (strong). On the other hand, the corresponding nonlabelled double-stranded oligonucleotide whose sequence is mutated (AGGTCA→AGGCAG) (hCIIITaTaKO) does not reduce the formation of this complex. A specific gel retardation is also obseved when the labelled oligonucleotide used as probe corresponds to the half-site AGGTCA present at the level of the site of the TaTa box of the human apo C-III gene (hCIII-TaTaWT) (FIG. 8).

In this figure, the −34/−10 fragment (probe hCII-ITaTaWT) of the promoter of the human gene for apo C-III was phosphorylated at the 5' ends by poly-nucleotide kinase in the presence of $[\gamma\text{-}^{32}P]$ATP. This probe was incubated in the presence of reticulocyte lysate (TNT-T7, Promega) programmed to express the hRORα1 receptor according to the protocol defined by the manufacturer or in the presence of control lysate.

The DNA/protein complexes were then separated on non denaturing polyacrylamide gel. After drying, the gel is subjected to autoradiography. The first lane of the gel corresponds to the migration of the probe incubated in the presence of the control lysate. The other lanes correspond to the migration of the probe incubated in the presence of lysate programmed to express hRORα1. A molar excess (10, 50, 100x) of the nonlabelled double-stranded oligonucleotides indicated was preincubated with the programmed lysate for 15 minutes before the addition of the probe.

The intensity of the retarded complex is reduced by competition with the homologous nonlabelled double-stranded oligonucleotide, by nonlabelled double-stranded oligonucleotides whose sequences correspond to the site of attachment of hRORα1 on the promoter of the rat apo AI gene (rAITaTaWT) (site to which hRORα1 is known to bind at high affinity (Vu-Dac et al., 1997, J. Biol. Chem., 272, 22401–22404)) or of the hRORα1 consensus response element (RORECons). The nonlabelled double-stranded oligonucleotide whose sequence corresponds to the mutated AGGTCA half-site hCIIITaTaKO (AGGCAG) (FIG. 8) situated downstream of the TaTa box of the apo C-III gene is inactive. A specific but weak gel retardation is also observed on the DNA fragment between positions −62 and −109 required to observe activation of the expression of the reporter gene by hRORα1 in transient transfection experiments (FIG. 9).

In this figure, fragments −34/−10 (probe HCIIITaTaWT) of the promoter of the human gene for apo C-III was phosphorylated at the 5' ends by polynucleotide kinase in the presence of $[\gamma\text{-}^{32}P]$ATP. These probes were incubated in the presence of reticulocyte lysate (TNT-T7, Promega) programmed to express the hRORα1 receptor according to the protocol defined by the manufacturer or in the presence of control lysate. The DNA/protein complexes were then separated on a nondenaturing polyacrylamide gel. After drying, the gel is subjected to autoradiography.

More precisely, this retardation appears to be attributable to the site between positions −82 and −70 (hCIII-C3PDR1) (FIG. 10).

In this figure, fragment −90/−64 of the promoter of the human gene for apo C-III was phosphorylated at the 5' ends with polynucleotide kinase in the presence of $[\gamma\text{-}^{32}P]$ATP. This probe was incubated in the presence of reticuloycte lysate ("TNT-T7", Promega) programmed to express the hRORα1 receptor according to the protocol defined by the manufacturer or in the presence of control lysate. The DNA/protein complexes were then separated on nondenaturing polyacrylamide gel. After drying, the gel is subjected to autoradiography. The first lane of the gel corresponds to the migration of the probe incubated in the presence of control lysate. The other lanes correspond to the migration of the probe incubated in the presence of lysate programmed to express hRORα1. A molar excess (10, 50, 100x) of the indicated nonlabelled double-stranded oligonucleotides was pre-incubated with the programmed lysate for 15 minutes before addition of the probe.

This retardation is specific: competition appears with the oligonucleotide whose sequences correspond to the hRORα1 consensus response element (RORECons) or to the half-site of the TaTa box of the human apo C-III gene (hCIIITaTaWT) (FIG. 10). Competition with the homologous nonlabelled oligo-nucleotide is also observed (FIG. 10).

In conclusion, the gel retardation experiments confirm the interaction of hRORα1 with the portion between positions −198 and +24 of the apo C-III promoter and suggest the existence of two binding sites: the half-site AGGTCA situated downstream of the TaTa box (−23/−18) and the half-site AGGTCA present in 5' of the C3P site (−77/−82).

c. Analysis of the Point Mutants of the Promoter of the Human Apo C-III Gene

In order to validate the results obtained with the deletion mutants and with the gel retardation technique, the construct −1415/+24hCIIIWTLuc+ was mutated by site-directed mutagenesis at the level of the half-site AGGTCA present downstream of the TaTa box of the gene for apo C-III (−23/−18) and/or at the level of the two half-sites AGGTCA of the C3P site (−70/−82).

In FIG. 11, 10,000 RK13 cells were plated per well of a 24-well culture plate and transfected with the aid of a cationic lipid with 50 ng/well of reporter vectors −1415/+24hCIIIWT-Luc+(noted WT), −1415/+24hCIIIC3P5'KO-Luc+(noted C3P5'KO), −1415/+24hCIIIC3P3'KO-Luc+ (noted C3P3'KO), −1415/+24hCIIIC3P5'+3'KO-Luc+(noted C3P5'+3'KO), −1415/+24hCIIITaTaKO-Luc+(noted TaTaKO), −1415/+24hCIIITaTa+C3P5'KO-Luc+(noted TaTa+C3P5'KO) and −1415/+24hCIIITaTa+C3P 3'KO-Luc+ (noted TaTa+C3P3'KO) as indicated, 100 ng/well of expression vector pCDNA3 or pCDNA3-hRORα1 as indicated and 50 ng of vector pSV-βgal. The total quantity of transfected DNA was brought to 500 ng/well with the aid of the plasmid pBluescript used as carrier. After incubating 36 hours, the cells were rinsed, lysed and the luciferase activity of the cellular extracts assayed with the aid of the "Dual-Luciferase™ Reporter Assay System" kit from Promega. The β-galactosidase activity of the cellular extracts was measured according to the conventional protocol (31).

FIG. 11 indicates that the mutation of the half-site AGGTCA present at position 3' of the C3P site (−77/−82) (construct −1415/+24hCIIIC3P3'KOLuC+) significantly reduces the sensitivity to hRORα1 of the promoter of the human apo C-III gene. In addition, whereas the single mutation of the half-site AGGTCA present downstream of the TaTa box (construct −1415/+24hCIIITaTaKOLuc+) does not affect the sensitivity of the promoter to the action of hRORα1, the combination of the same mutation with the mutation of the half-site AGGTCA present at position 3' of the C3P site (construct −1415/+24hCIIITaTa+C3P3'KOLuc+) appears to accentuate the loss of sensitivity of the promoter with respect to hRORα1.

d. Analysis of the Response Elements Isolated From the Apo C-III Promoter Cloned Upstream of the TK Promoter In FIG. 12, 10,000 RK13 cells were plated per well of a 24-well culture plate and transfected with the aid of a cationic lipid with 50 ng/well of reporter vectors (−30/−15)$_n$TkpGL3, (−76/−100)$_{2x}$TkpGL3, (−27/−59)$_{5x}$TkpGL3, (−59/−27)$_{8x}$TkpGL3, −47/−79)TkpGL3 and TkpGL3 (negative control) as indicated, 100 ng/well of expression vector pCDNA3 or pCDNA3-hRORα1 as indicated and 50 ng of vector pSV-βgal. The total quantity of transfected DNA was brought to 500 ng/well with the aid of the plasmid pBluescript used as carrier. After incubating 36 hours, the cells were rinsed, lysed and the luciferase activity of the cellular extracts assayed with the aid of the "Dual-Luciferase™ Reporter Assay System" kit from Promega. The β-galactosidase activity of the cellular extracts was measured according to the conventional protocol (31).

The FIG. 12 shows that the half-site AGGTCA present downstream of the TaTa box of the apo C-III gene cloned upstream of the Tk promoter (construct (−30/−15)hCIIITk-pGL3) is activable by hRORα1. Outside the context of the human apo C-III promoter, this site which is identified by gel retardation is functional. The construct which comprises two copies of the fragment −76/−100 (half-site AGGTCA 3' of the C3P site included) (construct (−76/−100)$_{2x}$hCIIITk-pGL3) cloned before the Tk promoter is also activated by hRORα1. The constructs which comprise other fragments of the proximal promoter of human apo C-III between the TaTa box and the C3P site cloned before the Tk promoter are insensitive to hRORα1.

e. Conclusions

At least one site which is essential for the action of hRORα1 on the promoter of the human apo C-III gene has been clearly identified: the half-site AGGTCA situated at position 3' of the C3P site (−77/−82). The role of the half-site oresent downstream of the TaTa box is difficult to evaluate in the light of the results presented. The presence of other hRORα1 response elements or of sites to which other nuclear factors capable of interacting with hRORα1 bind is suggested by the loss of sensitivity to hRORα1 which is observed when the fragment −1415/−198 is removed from the apo C-III promoter.

7. Novelty of the Action of hRORα1

In FIG. 13, the RK13 cells were plated on 60-mm culture plates and transfected at 50–60% confluence by the calcium phosphate technique with 500 ng/plate of reporter vector −1415/+24hCIIIWT-CAT (noted −1415/+24WTCAT), −198/+24hCIIIWT-CAT (noted −198/+24WTCAT), −2051/+26hAIWT-CAT (noted −2051/+26hAICAT) (human apo AI promoter), hAITaTakCAT (TaTa box of the human apo AI gene cloned before the Tk promoter), RORETkCAT (consensus ROR response element (monomeric) cloned upstream of the Tk promoter) or pBLCAT4 as indicated, 1 µg/plate of expression vector pSG5 (negative control) or pSG5-hRORα1 as indicated and 100 ng/plate of plasmid pCMV-βgal used as control for transfection efficiency. After incubating for 36 hours, the cells were rinsed, lysed and the CAT and β-galactosidase activity of the cellular extracts measured according to conventional protocols (31).

FIG. 13 indicates that the effect of hRORα1 is specific for the human gene for apo C-III: the human apo A-I promoter is not significantly affected contrary to what is described in rats (53). The sequence of the portion of the human apo AI promoter which flanks the TaTa box is different compared with the equivalent portion of the rat promoter. FIG. 13 shows that this portion of the human Promoter of apo A-I is insensitive to hRORα1. The modulation of the expression or of the activity of hRORα1 is therefore capable of differentially affecting the expression of the human genes encoding apo C-III or apo A-I respectively. The substances capable of modulating the activity of hRORα1 will consequently have an action at the level of the triglycerides which is dissociated from their action on the plasma HDL-cholesterol level. Such substances will therefore have a novel pharmacological profile.

8. Effects of the Isoforms of hROR

FIG. 14 shows, surprisingly, that the isoforms hRORα1, hRORα2 and hRORα3 all activate the construct −1415/+24hCIIIWTLuc+. This observation is in contrast with the absence of hRORα2 on the rat apo A-I promoter (53).

In this figure, the RK13 cells were plated on 60-mm culture plates and transfected at 50–60% confluence by the calcium phosphate technique with 500 ng/plate of reporter vector −1415/+24hCIIIWT-Luc+, 1 μg/plate of expression vector pCMX (negative control), pCMX-hRORα1, pCMX-hRORα2 or pCMX-hRORα3 as indicated, and 100 ng/plate of plasmid pCMV-βgal used as control for transfection efficiency. After incubating for 36 hours, the cells were rinsed, lysed and the luciferase and β-galactosidase activity of the cellular extracts measured according to conventional protocols (31).

9. Disruption of the RORα gene in the sg/sg Staggerer Mice is Associated with a Reduced Expression of apo C-III in the Liver of these Animals In FIG. 15, the hepatic expression of the apo C-III gene in the sg/sg mutant mice (carrying a truncated and nonfunctional RORα gene) is compared with the corresponding expression in the SG/SG wild-type mice by Northern blotting according to the protocol described before (32). The messenger RNA encoding murine apo C-III is visualized with the aid of a cDNA probe encoding rat apo C-III labelled using random hexamers as Primer (Boehringer Mannneim). The 36B4 cDNA clone encoding the human acidic ribosomal phospho-protein PO (34) whose expression is constant is used as quantification control.

FIG. 15 shows that the expression of the mouse apo C-III gene is considerably reduced in the liver of sg/sg mutant mice deficient in the RORα gene compared with SG/SG mice. The expression of the SB34 control gene is not affected by the mutation. This result confirms the physiological relevance of the observations described above and suggests that the RORα gene is also important for the expression of apo C-III in the liver of rodents.

10. Relevance of the Proposed Screening Methods

The activation (FIGS. 1 to 6, 11, 13 and 14) of the expression of the reporter gene cloned down-stream of the promoter of the human gene for apo C-III when the exogenous expression of hRORα1 is artificially increased based on the relevance of the use of this method to identify substances capable of modulating the activity of hRORα1.

FIG. 12 establishes the appropriateness of using the isolated sites cloned upstream of the Tk promoter before a reporter gene in order to identify substances capable of modulating the activity of hRORα1. A construct comprising three copies of the following site: 5′-GGAAAAGTGTGT-CACTGGGGCACG-3′ cloned before the Tk promoter has been characterized (FIG. 16).

In this figure, 10,000 RK13 cells were plated per well of a 24-well culture plate and transfected with the aid of a cationic lipid with 50 ng/well of reporter vectors (RevDR2) $_{3x}$TkLuc+, (RevDR2 m3′)-TkLuc+(half-site 3′ of the mutated DR2) or TkLuc+ (negative control) as indicated, 100 ng/well of expression vector pCDNA3 or pCDNA3-hRORα1 as indicated and 50 ng of vector pSV-βgal. The total quantity of transfected DNA was brought to 500 ng/well with the aid of the plasmid pBluescript used as carrier. After incubating for 36 hours, the cells were rinsed, lysed and the luciferase activity of the cellular extracts assayed with the aid of the "Dual-Luciferase™ Reporter Assay System" kit from Promega. The β-galactosidase activity of the cellular extracts was measured according to the conventional protocol (31).

Its sensitivity to hRORα1 is increased. This justifies its importance for screening substances capable of modulating the activity of the native hRORα1 nuclear receptor.

Finally, FIG. 17 establishes the appropriateness of using chimeras which combine the DNA binding domain of the yeast transcription factor Gal4 and the ligand binding domain of hRORα1 and of a reporter vector which comprises 5 copies of a Gal4 response element in order to identify substances capable of modulating the activity of hRORα1.

In FIG. 17, 10,000 RK13 cells were plated per well of a 24-well culture plate and transfected with the aid of a cationic lipid with 100 ng/well of reporter vector pG5TkpGL3, 0 to 100 ng/well of expression vector pGal4-+ or pGal4-hRORαDEF (supplemented with the plasmid pCDNA3 in order to maintain the number of transcription units constant) as indicated and 50 ng of vector pSV-βgal. The total quantity of transfected DNA was brought to 500 ng/well with the aid of the plasmid pBluescript used as carrier. After incubating for 36 hours, the cells were rinsed, lysed and the luciferase activity of the cellular extracts assayed with the aid of the "Dual-Luciferase™ Reporter Assay System" kit from Promega. The β-galactosidase activity of the cellular extracts was measured according to the conventional protocol (31).

REFERENCES

1. Cury M. D., McConathy W. J., Fesmire J. D., Alaupovic P. 1980. Quantitative determination of human apolipoprotein C-III by electroimmunoassay. *Biochim. Biophys. Acta.* 617:503–513.
2. Schonfeld G., Georges P. I., Miller J., Reilly P., Witztum J., 1979. Apolipoprotein C-Il and C-III levels in hypolipoproteinemia Metabolism.28:1001–1009
3. Stocks J., Holdsworth G, Galton D. J. 1979. Hypertriglycerideamia associated with an abnormal trigycerid rich lipoprotein carrying excess apolipoprotein C-III. Lancet. ii:667–671.
4. LA N. A., Gibson J. C., Ginsberg H. N. 1998. Independent regulation of plasma apolipoprotein C-II and C-III concentrations in very low density and high density lipoproteins: implications for the regulation of the catabolism of these lipoproteins. *J. Lipid. Res.* 29:669–677.

5. Luc G., Fievet C. Arveiler D., Evans A., Bard J. M., Cambien F., Fruchart J. C., Ducimetiere P. 1996. Apolipoproteins C-III and E in apo B and non apo B containing lipoproteins in two populations at cotasting risk for myocardial infarction: the ECTIM study. *J. Lipid Res.* 31: 508–517.
6. Malmendier C. L., Lontie J. F., Deicroix C., Dubois Y., Magot T., DeRoy. 1989. Apolipoproteins C-II and C-II metabolism in hypertriglyceridemic patients. Effects of a drastic triglyceride reduction by combined diet restriction and fenofibrate administration. *Atherosclerosis.* 77:139–149.
7. Ginsberg H. N., Le N. A., Goldberg I. J., Gibson J. C. Rubinstein A., Wang-Iverson P., Norum R., Brown W. V. 1986. Apolipoprotein B metabolism in subjects with deficiency of apolipoprotein C-III and A-I: evidence that apolipoprotein C-III inhibits catabolism of triglycerid-rich lipoproteins by lipoprotein lipase in vivo. *J. Clin. Invest:.* 78:1287–1295.
8. Dammerman M, Sandkuijl L. A., Halaas J. L., Chung W., Breslow J. L. 1993 An apolipoprotein C-III haplotype protective against hypertriglyceridemia is specified by promoter and $_3$' untranslated region polymorphisms. *Proc. Natl. Acad. Sci. USA.* 90:4562–4566.
9. Rees A. C., Shoulders C. C., Stocks J., Galton D. J., Baralle F. E. 1983. DNA polymorphism adjacent to human apolipoprotein A-I gene: relation to hypertriglyceridemia. *Lancet. i:* 444–446.
10. Maeda N., Li H., Lee D., Oliver P., Quarfordt S. H., Osada J. 1994. Targeted disruption of the apolipoprotein C-III gene in mice results in hypertriglyceridemia and protection from postprandial hypertriglyceridemia. *J. Biol. Chem.* 269:23610–23616.
11. Ito Y., Azrolan N., O'Connel A., Walsh A., Breslow J. L. 1990. Hypertriglyceridemia as a result of human apo C-III gene expression in transgenic mice. *Science.* 249:790–793.
12. De Silva H. V., Lauer S. J., Wang J., Simonet W. S., Weisgraber K. H., Mahley R. W., Taylor J. M. 1994. O*verexpression* of human apolipoprotein C-III in transgenic mice results in an accumulation of apolipoprotein B48 remnants that is corrected by excess apolipoprotein E. *J. Biol. Chem.* 269:2324–2335.
13. Aalto-Setalä,i K., Fisher E. A., Chen X., Chaek-Shaul T., Hayek T., Zechner R., Walsh A., Ramakrishnan R., Ginsberg H. N., Breslow J. L. 1992. Mechanism of hypertriglyceridemia in human apolipoprotein C-III transgenic mice. Diminished very low density lipoprotein fractional catabolic rate associated with increased apo C-III and reduced apo E on the particles. *J. Clin. Invest:.* 90:1889–1900.
14. Clavey V., Lestavel-Delattre S., Copin C., Bard T. M., Fruchart J. C. 1995. Modulation of lipoprotein B binding to the LDL receptor by exogenous lipids and apolipoproteins C-I, C-II, C-III and E. *Arterioscler. Throm. Vasc. Biol.* 15:963–971.
15. Aalto-Setala K., Weinstock P. H., Bisgaier C. L., Wu L., Smith J. D., Breslow J. L. 1996. Further characterization of the metabolic properties of triglycerid rich lipoproteins from human and mouse apo C-III transgenic mice. *J. Lipid Res.* 37:1802–1811.
16. Ebara T., Ramakrishnan R., Steiner G., Shachter N. S. 1997. Chylomicronemia due to apolipoprotein C-II overexpression in apolipoprotein E-null mice. Apolipoprotein C-III induced hypertriglyceridemia is not mediated by effects on apolipoprotein E. *J. Clin. Invest.* 99:2672–2681.
17. Giguere V., Tini M., Flock G., Ong E., Evans R. M., Otulakowski G. 1994. Genes Dev. 3:538–553.
18. Becker-André, M., Andre, E., DeLamarter J. F. 1993. *Biochem. Biophys. Res. Commun.* 194:1371–1379.
19. Carlberg C., van Huijsduijnen R., Staple J. K., DeLamarter J. F., and Becker-André, M. 1994. Mol. *Endocrinol.* 8: 757–770.
20. Hirose T;, Smith R. J. and Jetten A. M. 1994. Biochem. Biophys. Res. Commun. 205:1976–1983.
21. Forman B. M., Chen J., Blumberg B., Kliewer S. A., Henshaw R., Ong E. S., Evans R. M. 1994. Mol. Endocrinol. 8:1253–1260.
22. Giguére V., McBroom L. D. B., and Flock G. 1995. Mol. Cell. Biol. 15:2517–2526.
23. Herrup K. and Mullen R. J. 1979. Regional variation and absence of large neurors in the cerebellum of the staggerer mouse. *Brain Res.* 172: 1–12.
24. Shojaeian-Zanjani H., Herrup K., Guastavino J. M., Delhaye-Bouchaud N., and Mariani J. 1994. Development studies of the inferior olivary nucleus in the staggerer mutant mice. De. Brain. Res. 82: 18–28.
25. Trenkner E., and Hoffman N. K. 1986. Defective development of the thymus and immunological abnormalities in the neurological mouse mutation staggerer. J. Neurosci. 6: 1733–1737.
26. Kopmels B., Mariani J., Delhaye-Boucnaud N., Audibert F., Fradelizi D., and Wollman E. E. 1992. Evidence for a hyperexcitability stage of the staggerer mutant mice macrophages. J. Neurochem. 58:192–199.
27. Hamilton B. A., Frankel W. N., Kerrebrock A. W., Hawkins T. L., FitzHugh W., Kusumi K., Russel L. B., Mueller K. L., van Berkel V., Birren B. W., Kruglyak L. and Lander E. S. 1996. Disruption of the nuclear hormone receptor RORα in staggerer mice. Nature. 379:736–739.
28. Pagen B., Ishida B. Y., Verstuyft J., Winters R. B. and A L bee D. 1990. Atherosclerosis susceptibility differences among progenitors of recombinant inbred strains of mice. Arteriosclerosis. 10: 316–323.
29. Luckow B., and Schutz G. 1987. CAT constructions with multiple unique restriction sites for the functional analysis of eukaryotic promoters and regulatory elements. Nucl. Acids Res. 15:5490.
30. Mc Gregor G. R. and Caskey C. T. 1989. Construction of plasmids that express *E. coli*-galactosidase in mammalian cells. Nucl. Acids Res. 17:2365.
31. Ausubel F. Brent R., Kingston R., Moore D., Smith J., Seidman C., Struhl K. 1987. Current protocols in molecular biology, Greene Publishing—Wiley Interscience, New York.
32. Staels B., Vu-Dac N., Kosykh R, Saladin R., Fruchart J. C., Dallongeville J. and Auwerx J. 1995. Fibrates dowregulate apolipoprotein C-III expression independent of induction of peroxisomal Acyl Coenzyme A oxidase. J. Clin. Invest. 95:705–712.

33. Masiakowski P., Breathnach R., Bloch J., Gannon F., Krust A., ans Chambon P. 1982. cloning of cDNA sequences of hormone-regulated genes from MCF-7 human breast cancer cell line. Nucl. Acid Res. 10:7895–7903
34. Laborda J. 1991. 36B4 c DNA used as an estradiol-independent mRNA control is the cDNA for human acidic ribosomal phosphoprotein PO. Nucl. Acid Res.19:3998.
35. Staels B., and Auwerx J. 1992. Perturbation of developmental gene expression in rat liver by fibric acid derivatives: lipoprotein lipase and alpha-fetoprotein as models. Development. 115: 1035–1043.
36. Harding H. P. and Lazar M. A. 1993. The orphan receptor Rev-Erba activates transcription via a novel response element. Mol. Cell. Biol. 13: 3113.
37. Harding H. P. and Lazar M. A. 1995. The monomer-binding orphan receptor Rev-ErbA_represses transcription as a dimer on a novel direct repeat. Mol. Cell. Biol. 15: 4791.
38. Harding H. P. and Lazar M. A. 1993. The orphan receptor Rev-Erba activates transcription via a novel response element. Mol. Cell. Biol. 13: 3113.
39. Dumas B., Harding H. S., Choi K., Lehman M., ChungM., Lazar M. A., Moore D. 1994. A new orphan member of the nuclear hormone receptor superfamily closely related to Rev-Erb. Mol. Endocrinol. 8:996.
40. Forman B., Chen J., Blumberg B., Kliewer S. A., Hensaw R., Ong E. S., Evans R. Cross-talk among RORα and the Rev-Erb family of nuclear receptor. Mol. Endocrinol. 3:1253.
41. Giguere V., Mc Broom L., Flock G.1995. Determinants of target gene specificity for RORα monomeric DNA binding by an orphan nuclear receptor. Mol. Cell. Biol.15: 2517.
42. Krey G, Braissant O, LiHorest F, kalkhoven E, Perroud M, Parker M, Wahli W. 1997. Fatty acids, Eicosanoids, and hypolipidemic agents identified as ligands of peroxisome proliferator-activated Receptors by coactivator-dependent Receptor Ligand Assay. Mol. Endocrinol: 779–791
43. Harding H P, Atkins G B, Jaffe A B, Seo W J, Lazar M A, 1997. Transcriptional activation and repression by RORα, an orphan nuclear receptor required for cerebellar development. Mol. Endocrinol. 11:1737–1746
44. Molten F 1994, Drug sensitivity (suicide) genes for selective cancer chemotherapy. Cancer Gene Ther. 1: 125–134
45. Sadowski I, Ma J. Triezenberg S, Ptashme M. 1988. Gal4-VP16 is an unusually potent transcriptional activator. Nature 335:563–564
46. Webster et ai., 1998. Cell. 52:169–178
47. Giguere V, Tini M, Flock G, Ong E, Evans R M, Otulakowski G. 1994. Isoform-specific amino-terminal domains dictate DNA-binding properties of RORα, a novel family of orphan nuclear receptors Genes Dev. 8:538–553
48. Vanacker J M, laudet V, Adelmant G, stéhelin D, Rommelaere J. 1993. Interconnection between thyroid hormone receptor signalling pathways and parvovirus cytotoxic functions. J. Virol. 67:7668–7672
49. Vu-Dac N, Schoonjans K, Laine B, Fruchart J C, Auwerx J, staels B. 1994. Negative regulation of the human apolipoprotein A-I promoter by fibrates can be attenuated by the interaction of the peroxisome proliferator-activated receptor with its response element. J. Biol. chem. 269: 31012–31018
50. Fried M G, Crothers D M. 1983. CAP and RNA polymerase interactions with the lac promoter:binding stoichiometry and long range effects. Nucl. Acids res. 11:141–158
51. Becker-André, M, Wiesenberg I, schaeren-Wiemers N, Andre E, Missbach M, Saurat J H, Carlberg C. pineal gland hormone melatonin binds and activates an orphan of the nuclear receptor superfamily. J. Biol. Chem. 1994, 269: 28531–4
52. Becker-André, M, Wiesenberg I, schaeren-Wiemers N, Andre E, Missbach M, Saurat J H, Carlberg C.pineal gland hormone melatonin binds and activates an orphan of the nuclear receptor superfamily., J. Biol. Chem., 272, 26, page 16707
53. Vu-Dac N., Gervois P., Grotzinger T., De vos P., Schoonjans K., Frucnart J. C., Auwerx J., Mariani J., Tedgui A., Staels B., Transcriptional Regulation of apo A-I gene expression by nuclear receptor ROR alpha, J. Biol. Chem., 1997, vol 272, Iss 36, pp 22401–22404
54. Mamontova A, Seguret-Mace S, Esposito B, Chaniale C, Bouly M, Delhaye-Bouchaud N, Luc G, Staels B, Duverger N, Mariani J, Tedgui A severe atherosclerosis and hypoalpha lipoproteinemia in the staggerer mouse, a mutant of the nuclear receptor ROR alpha, Circulation, 98, 2738–2743, 1998
55. Masucci-Magoulas L, Goldberg I J, Bisgaier C L, Serajuddin H, Francone O L, Breslow J L, Tall A R, A Mouse Model with Features of Familial Combined Hyperlipidemia, Science, 1997, 275, 391–394
56. Hodis and Mack, 1998, Eur. Heart J., suppl.19 A40–44
57. Assman G, Schulte H, Culien P, New and classical risk factors—the munster heart study (PROCAM), 1997, Eur. J. Med. Res. 2, 237–242
58. Austin, 1991, Arterioscler. Thromb.11:2–14
59. Vu-Dac N, Schoonjans K, Kosykh V, Dallongeville J, Fruchart J C, Staels B, Auwerx J, Fibrates increase human apolipoprotein A-II expression through activation of the peroxisome proliferator-activated receptor, JCI, 96,741–750, 1995
60. Talianidis I, tambakaki A, Toursounova J, Zannis V I, Complex interactions between SP1 bound to multiple distal regulatory sites and HNF-4 bound to the proximal promoter lead to transcriptional activation of liver-specific human APOCIII gene, 1995, Biochemistry, 34, 10298–10309
61. Vu-Dac N, Gervois P, Torra I P, Fruchart J C, Kosykh V, Kooistra T, Princen H M, Dallongeville J, Staels B, Retinoids increase human Apo C-III expression at the transcriptional level via the retinoid X receptor. Contribution to the hypertriglyceridemic action of retinoids, JCI, 1998,102(3) 623–32

TABLE 1

| Name | Sequence | 5' terminus | 3' terminus | Use | Remarks |
|---|---|---|---|---|---|
| hC3F7 | 5'-GATCTCAGCAGGTGACCTTTGCCCAGCGCCC-3' | −90 | −64 | gel shift | |
| hC3R7 | 5'-GATCGGGCGCTGGGCAAAGGTCACCTGCTGA-3' | −64 | −90 | gel shift | |
| hC3F8 | 5'-GATCTGATATAAAACAGGTGCGAACCCTC-3' | −34 | −10 | gel shift | |
| hC3R8 | 5'-GATCGAGGGTTCTGACCTGTTTTATATCA-3' | −10 | −34 | gel shift | |
| hC3F12 | 5'-GATCGATATAAAACAGGCAGGAACCCTC-3' | −33 | −10 | gel shift | −20, −19, −18 |
| hC3R12 | 5'-GATCGAGGGTTCCTGCCTGTTTTATATC-3' | −10 | −33 | gel shift | −20, −19, −18 |
| hC3F15 | 5'-GATCCTCAGTGCCTGCTGCCCTGGAGATGATATAA-3' | −56 | −27 | cloning, gel shift | +BamHI site |
| hC3R15 | 5'-GATCTTATATCATCTCCAGGGCAGCAGGCACTGAG-3' | −27 | −56 | cloning, gel shift | +BglII site |
| hC3F17 | 5'-GATCCTTGCCCAGCGCCCTGGGTCCTCAGTGCCTGA-3' | −76 | −47 | cloning, gel shift | +BamHI site |
| hC3R17 | 5'-GATCTCAGGCACTGAGGACCCAGGGCGCTGGGCAAG-3' | −47 | −76 | cloning, gel shift | +BglII site |
| hC3F18 | 5'-ACGTGTCGACACTAGTGATAAAACAGGTCAGAAGATAAACAGGTCAGAAGATAAACAGG-3' | −53 | −15 | cloning | |
| hC3R18 | 5'-CGATGGTACCCTCGAGCAATGTGCTAGCTTCTGACCTGTTTTATCTTCTTCTGACCTGTTTTATC-3' | −15 | −33 | cloning | |
| hC3F20 | 5'-TCAGCAGGTGATGTTTGCCCAGCGCCC-3' | −90 | −64 | mutagenesis | −78, −79 |
| hC3R20 | 5'-GGGCGCTGGGCAAACATCACCTGCTGA-3' | −64 | −90 | mutagenesis | −78, −79 |
| hC3F21 | 5'-GATCTCATCTCCACTGGTCAGCAGGTGACCTTTGCCCAGCGCCCTG-3' | −102 | −62 | cloning, gel shift | +BglII site |
| hC3R21 | 5'-GATCCAGGGCGCTGGGCAAAGGTCACCTGCTGACCAGTGGAGATGA-3' | −62 | −102 | cloning, gel shift | +BamHI site |
| hC3F22 | 5'-ACGTGTCGACACTAGTAAGGTCACCTGCTGACCAGTGGAGAAAGGTCACCTGCTGACCAGTGG-3' | −76 | −100 | cloning | |
| hC3R22 | 5'-CGATGGTACCCTCGAGCAATGTGCTAGCTCTCCACTGGTCAGCAGGTGACCTTCTCCACTGG-3' | −100 | −76 | cloning | |
| hC3F29 | 5'-GGAGATGATATAAAACACACATGAACCCTCCTGCCTG-3' | −39 | −3 | mutagenesis | −22, −21, −20, −19, −18 |
| hC3R29 | 5'-CAGGCAGGAGGGTTCATGTGTGTTTTATATCATCTCC-3' | −3 | −39 | mutagenesis | −22, −21, −20, −19, −18 |
| hC3F30 | 5'-GGTCAGCAGGTGATGTTTGCAGAGCGCCCTGGGTCC-3' | −92 | −57 | mutagenesis | −71, −72, −78, −79 |
| hC3R30 | 5'-GGACCCAGGGCGCTCTGCAAACATCACCTGCTGACC-3' | −57 | −92 | mutagenesis | −71, −72, −78, −79 |
| hAIF1 | 5'-GATCCAGACATAAATAGGCCCCTGCAAGACA-3' | −105 | −81 | cloning, gel shift | +BamHI site |
| hAIR1 | 5'-GATCTGTCTTGCAGGGCCTATTTATGTCTG-3' | −81 | −105 | cloning, gel shift | ++BglII site |
| 82 | 5'-GATGGGATCCGCCAGGGTTTTCCCAGTCACGAC-3' | 4232 | 4282 | cloning | pBLCAT4 |
| 610 | 5'-GATCCACACATATATAGGTCAGGAAGAAGA-3' | −36 | −12 | cloning, gel shift | +BamHI site |
| 609 | 5'-GATCTCTTCTTCCCTGACCTATATATGTGTG-3' | −12 | −36 | cloning, gel shift | +BglII site |
| 613 | 5'-GATCTTGACCTACATTCTAAGCTG-3' | | | cloning, gel shift | +BglII site |
| 614 | 5'-GATCCAGCTTAGAATGTAGGTCAA-3' | | | cloning, gel shift | +BamHI site |
| 510 | 5'-TCGCCAAGCTTCTCGTGATCTGCGGCA-3' | 215 | 189 | cloning, gel shift | +HindIII site; pBLCAT4 |
| 512 | 5'-TATGCAGTTGCTCTCCAGCGGTTCCATCTTCC-3' | 169 | 138 | cloning, gel shift | pGL3 |
| 514 | 5'-CGACTCTAGAAGATCTTGCCCCGCCCAGCG-3' | 21 | 50 | cloning, gel shift | pBLCAT4 |
| 1129 | 5'-GATCCGGAAAAGTGTGTCACTGGGGCACGA-3' | | | cloning, gel shift | +BamHI site |
| 1142 | 5'-GATCTCGTGCCCCAGTGACACACTTTTCCG-3' | | | cloning, gel shift | +BglII site |
| 1126 | 5'-GATCTCGGCTAGGAGTGACACACTTTTCCG-3' | | | cloning, gel shift | +BglII site |
| 1132 | 5'-GATCCGGAAAAGTGTGTCACTCCTAGCCGA-3' | Table 1 | | cloning, gel shift | +BamHI site |

TABLE 2

Composition of the double-stranded oligonucleotides used in gel retardation

| Name | "sense" oligonucleotide | "antisense" oligonucleotide |
|---|---|---|
| hCIIITaTaWT | hCIIIF8 | hCIIIR8 |
| hCIIITaTaKO | hCIIIF12 | hCIIIR12 |
| hCIIIC3PDR1WT | hCIIIF7 | hCIIIR7 |
| hCIII(−62/−102) | hCIIIF21 | hCIIIR21 |
| RORECons | 613 | 614 |
| rATTaTaWT | 610 | 609 |

What is claimed is:

1. A method of screening a substance for usefulness in the treatment of a lipid metabolism dysfunction comprising contacting said substance with a response element of human RORα of the human apo C-III promoter involved in the regulation of the apo C-III gene, and measuring the level of apo C-III gene expression or the level of expression of a reporter gene placed under the control of a promoter comprising said response element.

2. The method of screening according to claim 1, wherein the reporter gene is chosen from chloramphenicol acetyltransferase, the gene for luciferase from firefly or from *Renilla*, the gene for secreted alakaline phosphatase, the gene for beta-galactosidase or the gene for apo C-III.

3. The method of screening according to claim 1, wherein the effect of said substance on the expression of said apo C-III or reporter gene is determined using transfection or analysis of mRNAs in vitro or on models in vitro or in vivo.

4. A method of measuring the expression of the apo C-III gene, comprising contacting a substance with a response element of the ROR α receptor of the apo C-III promoter and then measuring:

i) the binding of said substance to the response element; or ii) the modulation of the transcriptional activity of a gene placed under the control of a promoter comprising said response element.

5. A method of screening a substance for usefulness in the treatment of a lipid metabolism dysfunction comprising, contacting said substance with a response element of RORα of the apo C-III promoter involved in the regulation of the apo C-III gene, and and measuring the binding of said receptor to said response element.

6. A method of claim 5, wherein the measuring is performed by the gel retardation method.

7. A method of claim 1, wherein the level of apo C-III gene expression is measured.

8. A method of claim 1, wherein the level of a reporter gene expression is measured.

* * * * *

UNITED STATES PATENT AND TRADEMARK OFFICE
CERTIFICATE OF CORRECTION

PATENT NO. : 6,998,254 B1  Page 1 of 1
APPLICATION NO. : 09/646924
DATED : February 14, 2006
INVENTOR(S) : Eric Raspe It is certified that error appears in the above-identified patent and that said Letters Patent is hereby corrected as shown below:

On the Title page item (54) and col. 1, line 1, reads "FOR RECEPTORS FOR" should read -- FOR --

Column 28, line 19, reads "and measuring the" should read -- measuring the --

Signed and Sealed this

Twenty-ninth Day of July, 2008

JON W. DUDAS
*Director of the United States Patent and Trademark Office*